US010500106B2

(12) United States Patent
Zink, II et al.

(10) Patent No.: US 10,500,106 B2
(45) Date of Patent: Dec. 10, 2019

(54) METHODS FOR MAKING DIAPER PANTS WITH A DESIGN HAVING A DISCONTINUOUS REGION BETWEEN A BELT AND CHASSIS ARRANGED TO PROVIDE A CONTIGUOUS APPEARANCE

(71) Applicant: The Procter & Gamble Company, Cincinnati, OH (US)

(72) Inventors: Ronald Joseph Zink, II, Blue Ash, OH (US); Nelson Edward Greening, II, Cincinnati, OH (US); Linda Ann Sauer, Colerain Township, OH (US); John Joseph Litchholt, Lawrenceburg, IN (US); Jason Ashley Wagner, Lawrenceburg, IN (US); Sarah Nicole Wolfe, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 621 days.

(21) Appl. No.: 15/095,375

(22) Filed: Apr. 11, 2016

(65) Prior Publication Data
US 2016/0302977 A1    Oct. 20, 2016

Related U.S. Application Data

(60) Provisional application No. 62/147,004, filed on Apr. 14, 2015.

(51) Int. Cl.
*A61F 13/15*    (2006.01)
*A61F 13/49*    (2006.01)
(Continued)

(52) U.S. Cl.
CPC .. *A61F 13/49011* (2013.01); *A61F 13/15699* (2013.01); *A61F 13/15723* (2013.01);
(Continued)

(58) Field of Classification Search
CPC .......... A61F 13/15699; A61F 13/15723; A61F 13/15747; A61F 13/15804;
(Continued)

(56) References Cited

U.S. PATENT DOCUMENTS

| 2,075,189 A | 3/1937 | Galligan et al. |
| 3,025,199 A | 3/1962 | Harwood |

(Continued)

FOREIGN PATENT DOCUMENTS

| WO | WO 2006/017718 A1 | 2/2006 |
| WO | WO 2012/131502 A1 | 10/2012 |

(Continued)

OTHER PUBLICATIONS

PCT/US2016/027016 international Search report, dated Jul. 26, 2016, 10 pages.
All Office Actions, U.S. Appl. No. 15/095,416.

*Primary Examiner* — Sonya M Sengupta
(74) *Attorney, Agent, or Firm* — Charles R. Matson

(57) ABSTRACT

The present disclosure relates to absorbent articles and methods for assembling absorbent articles having a design including: a first graphic extending along a first component, a second graphic extending along a second component, and a discontinuous region separating the first graphic from the second graphic. The discontinuous region is configured to provide the appearance that the first and second graphics form a contiguous design while at the same time mitigating the need to precisely align the graphics on separated components to form a contiguous design during the assembly process.

16 Claims, 30 Drawing Sheets

(51) Int. Cl.
*B32B 37/14* (2006.01)
*B32B 38/00* (2006.01)
*A61F 13/496* (2006.01)
*A61F 13/551* (2006.01)

(52) U.S. Cl.
CPC .. *A61F 13/15747* (2013.01); *A61F 13/15804* (2013.01); *A61F 13/496* (2013.01); *A61F 13/5511* (2013.01); *B32B 37/14* (2013.01); *B32B 38/0004* (2013.01); *A61F 2013/15796* (2013.01); *B32B 2555/02* (2013.01)

(58) Field of Classification Search
CPC ............. A61F 13/49011; A61F 13/496; A61F 13/5511; A61F 2013/15796; B32B 2555/02; B32B 37/14; B32B 38/0004
USPC .................................. 156/239, 240, 250, 277
See application file for complete search history.

(56) References Cited

U.S. PATENT DOCUMENTS

| | | | |
|---|---|---|---|
| 3,848,594 A | 11/1974 | Buell | |
| 3,860,003 A | 1/1975 | Buell | |
| 4,107,364 A | 8/1978 | Sisson | |
| 4,209,563 A | 6/1980 | Sisson | |
| 4,515,595 A | 5/1985 | Kievit et al. | |
| 4,610,678 A | 9/1986 | Weisman et al. | |
| 4,662,875 A | 5/1987 | Hirotsu et al. | |
| 4,673,402 A | 6/1987 | Weisman et al. | |
| 4,695,278 A | 9/1987 | Lawson | |
| 4,704,115 A | 11/1987 | Buell | |
| 4,795,454 A | 1/1989 | Dragoo | |
| 4,834,735 A | 5/1989 | Alemany et al. | |
| 4,834,741 A | 5/1989 | Sabee | |
| 4,846,815 A | 7/1989 | Scripps | |
| 4,888,231 A | 12/1989 | Angstadt | |
| 4,894,060 A | 1/1990 | Nestegard | |
| 4,909,803 A | 3/1990 | Aziz et al. | |
| 4,946,527 A | 8/1990 | Battrell | |
| 5,151,092 A | 9/1992 | Buell et al. | |
| 5,167,897 A | 12/1992 | Weber et al. | |
| 5,221,274 A | 6/1993 | Buell et al. | |
| 5,330,458 A | 7/1994 | Buell et al. | |
| 5,360,420 A | 11/1994 | Cook et al. | |
| 5,562,646 A | 10/1996 | Goldman et al. | |
| 5,599,335 A | 2/1997 | Goldman et al. | |
| 5,628,097 A | 5/1997 | Benson et al. | |
| 5,643,588 A | 7/1997 | Roe et al. | |
| 5,669,894 A | 9/1997 | Goldman et al. | |
| 5,674,216 A | 10/1997 | Buell et al. | |
| 5,702,551 A | 12/1997 | Huber et al. | |
| 5,735,840 A | 4/1998 | Kline et al. | |
| 5,916,661 A | 6/1999 | Benson et al. | |
| 5,928,212 A | 7/1999 | Kline et al. | |
| 5,968,025 A | 10/1999 | Roe et al. | |
| 6,107,537 A | 8/2000 | Elder et al. | |
| 6,107,539 A | 8/2000 | Palumbo et al. | |
| 6,118,041 A | 9/2000 | Roe et al. | |
| 6,153,209 A | 11/2000 | Vega et al. | |
| 6,251,097 B1 | 6/2001 | Kline et al. | |
| 6,410,129 B2 | 6/2002 | Zhang et al. | |
| 6,426,444 B2 | 7/2002 | Roe et al. | |
| 6,432,098 B1 | 8/2002 | Kline et al. | |
| 6,545,197 B1 | 4/2003 | Muller et al. | |
| 6,586,652 B1 | 7/2003 | Roe et al. | |
| 6,617,016 B2 | 9/2003 | Zhang et al. | |
| 6,627,787 B1 | 9/2003 | Roe et al. | |
| 6,669,618 B2 | 12/2003 | Reising et al. | |
| 6,790,798 B1 | 9/2004 | Suzuki et al. | |
| 6,825,393 B2 | 11/2004 | Roe et al. | |
| 6,861,571 B1 | 3/2005 | Roe et al. | |
| 7,371,302 B2 | 5/2008 | Miyamoto et al. | |
| 7,569,039 B2 | 8/2009 | Matsuda et al. | |
| 7,587,966 B2 | 9/2009 | Nakakado et al. | |
| 8,440,043 B1 | 5/2013 | Schneider et al. | |
| 2004/0097895 A1 | 5/2004 | Busam et al. | |
| 2004/0158212 A1 | 8/2004 | Ponomarenko et al. | |
| 2005/0107764 A1 | 5/2005 | Matsuda et al. | |
| 2007/0078427 A1 | 4/2007 | Raycheck et al. | |
| 2007/0093769 A1 | 4/2007 | Kline et al. | |
| 2009/0312730 A1 | 12/2009 | LaVon et al. | |
| 2012/0061015 A1 | 3/2012 | LaVon et al. | |
| 2012/0061016 A1 | 3/2012 | LaVon et al. | |
| 2013/0072887 A1 | 3/2013 | LaVon et al. | |
| 2013/0211356 A1 | 8/2013 | Nishikawa et al. | |
| 2013/0255861 A1 | 10/2013 | Schneider | |
| 2013/0255862 A1 | 10/2013 | Schneider et al. | |
| 2013/0255863 A1 | 10/2013 | LaVon et al. | |
| 2013/0255864 A1 | 10/2013 | Schneider et al. | |
| 2013/0255865 A1 | 10/2013 | Brown et al. | |
| 2013/0270065 A1 | 10/2013 | Papsdorf et al. | |
| 2013/0270066 A1 | 10/2013 | Papsdorf et al. | |
| 2013/0270067 A1 | 10/2013 | Papsdorf et al. | |
| 2013/0270069 A1 | 10/2013 | Papsdorf et al. | |
| 2013/0306226 A1 | 11/2013 | Zink et al. | |
| 2014/0148773 A1 | 5/2014 | Brown et al. | |
| 2016/0302976 A1 | 10/2016 | Zink, II et al. | |

FOREIGN PATENT DOCUMENTS

| | | |
|---|---|---|
| WO | WO 2010/141302 A1 | 12/2012 |
| WO | WO 2015/134459 A1 | 9/2015 |
| WO | WO 2016/100501 A1 | 6/2016 |
| WO | WO 2016/100502 A1 | 6/2016 |

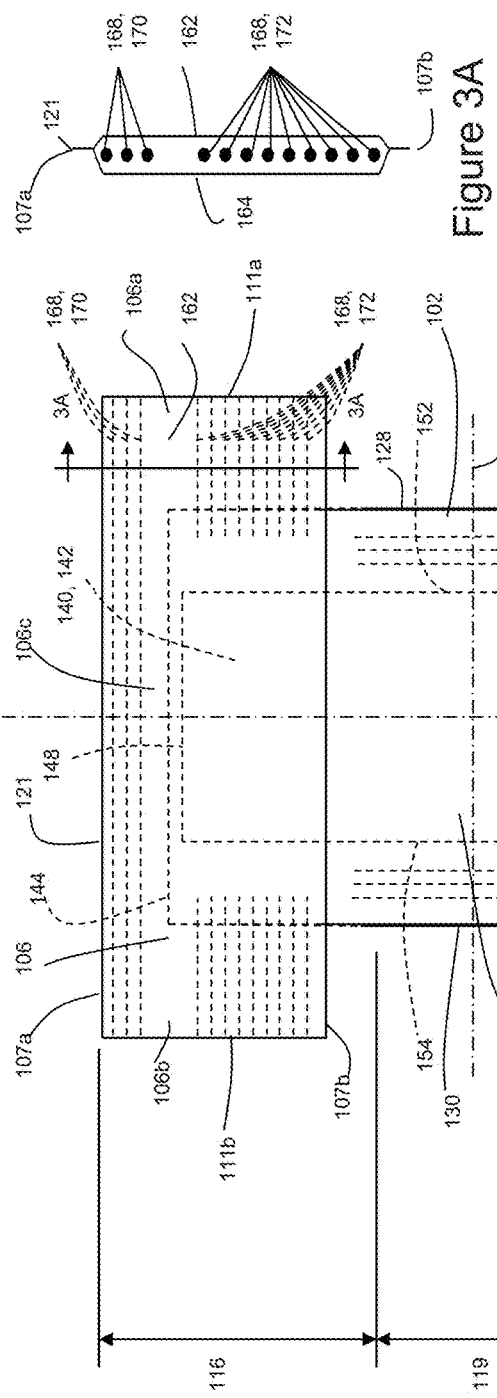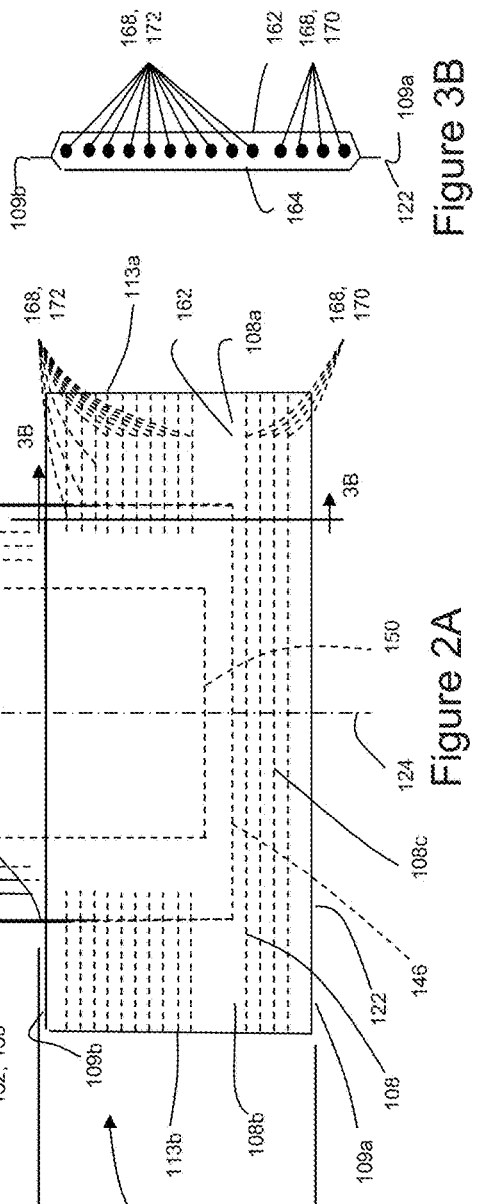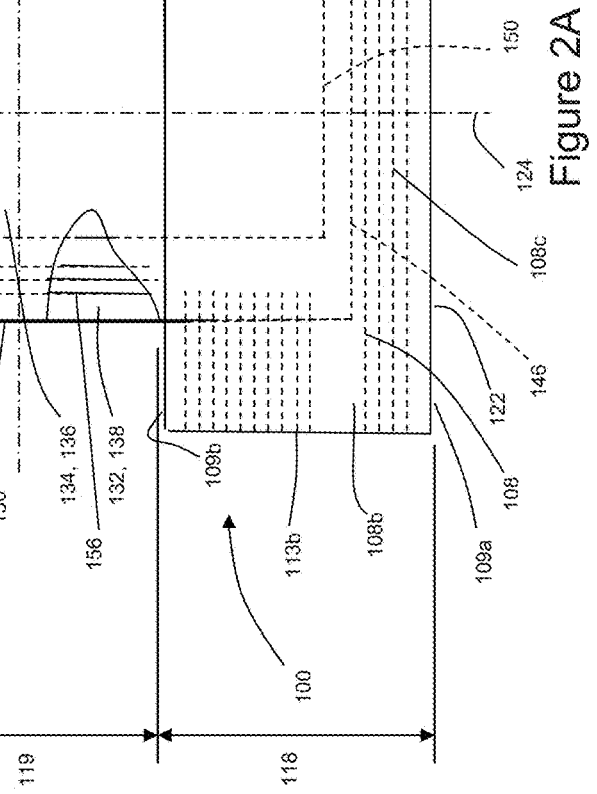

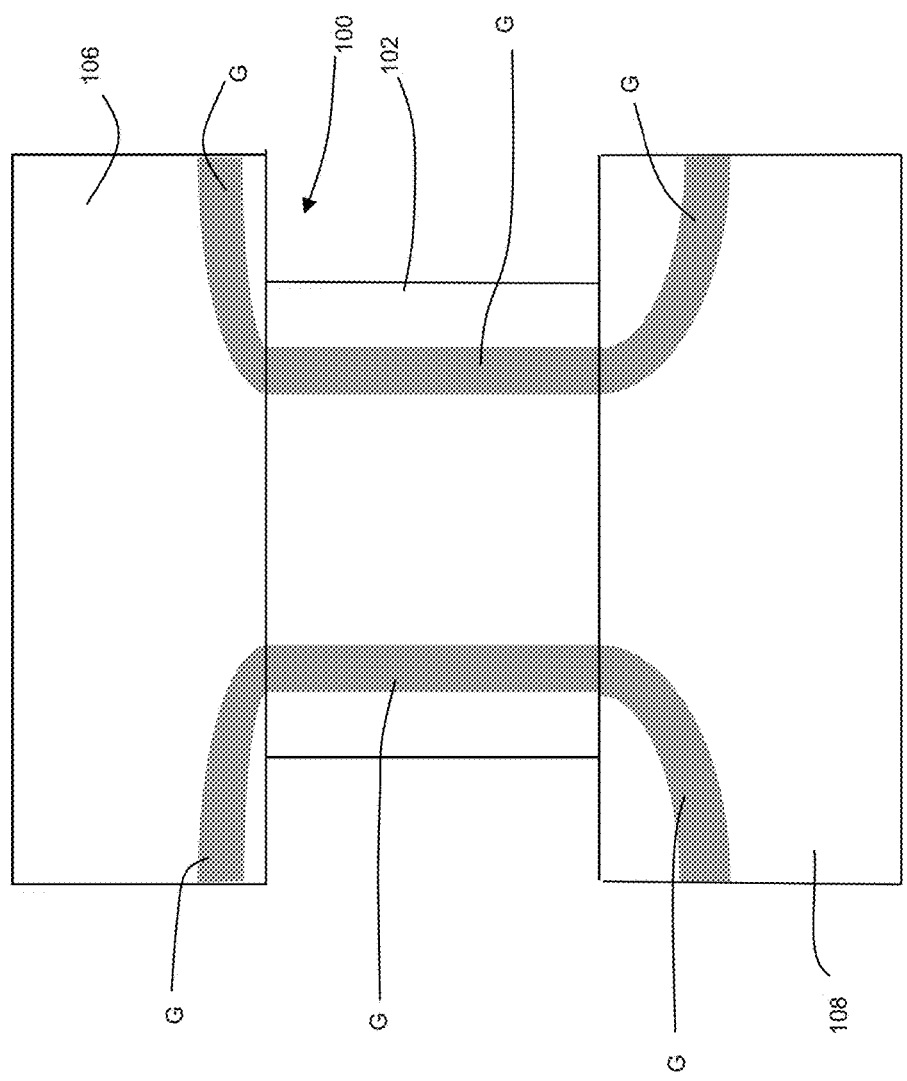
Figure 2B1

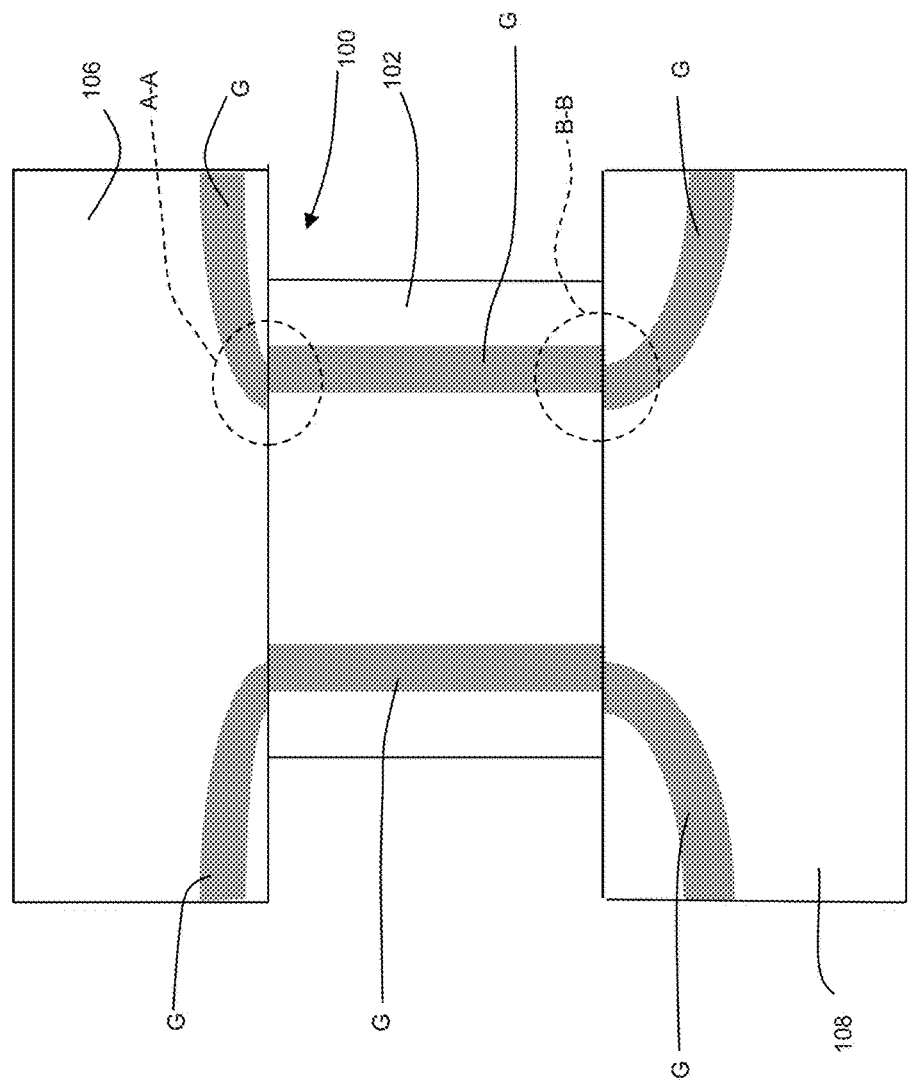
Figure 2B2

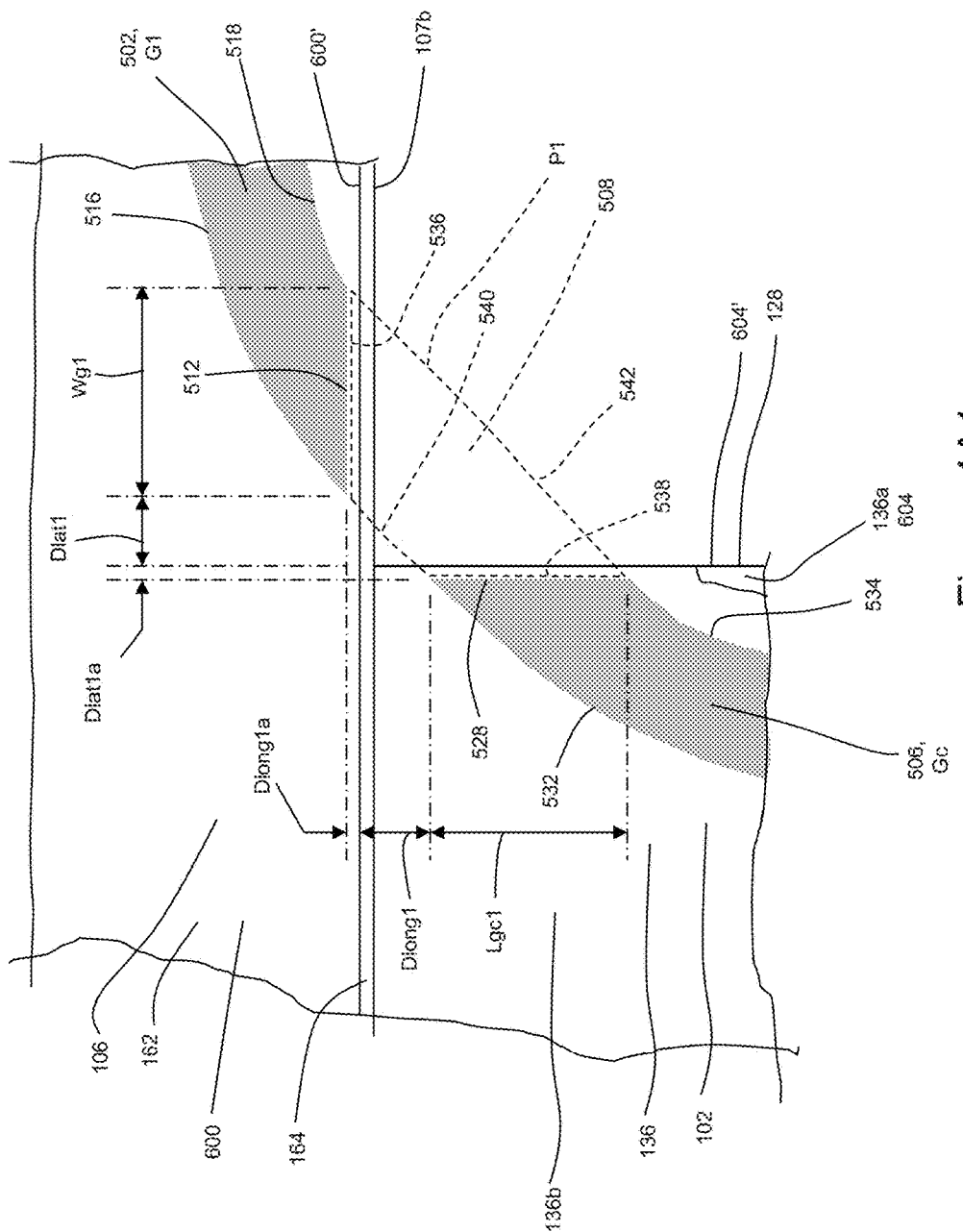
Figure 4A1

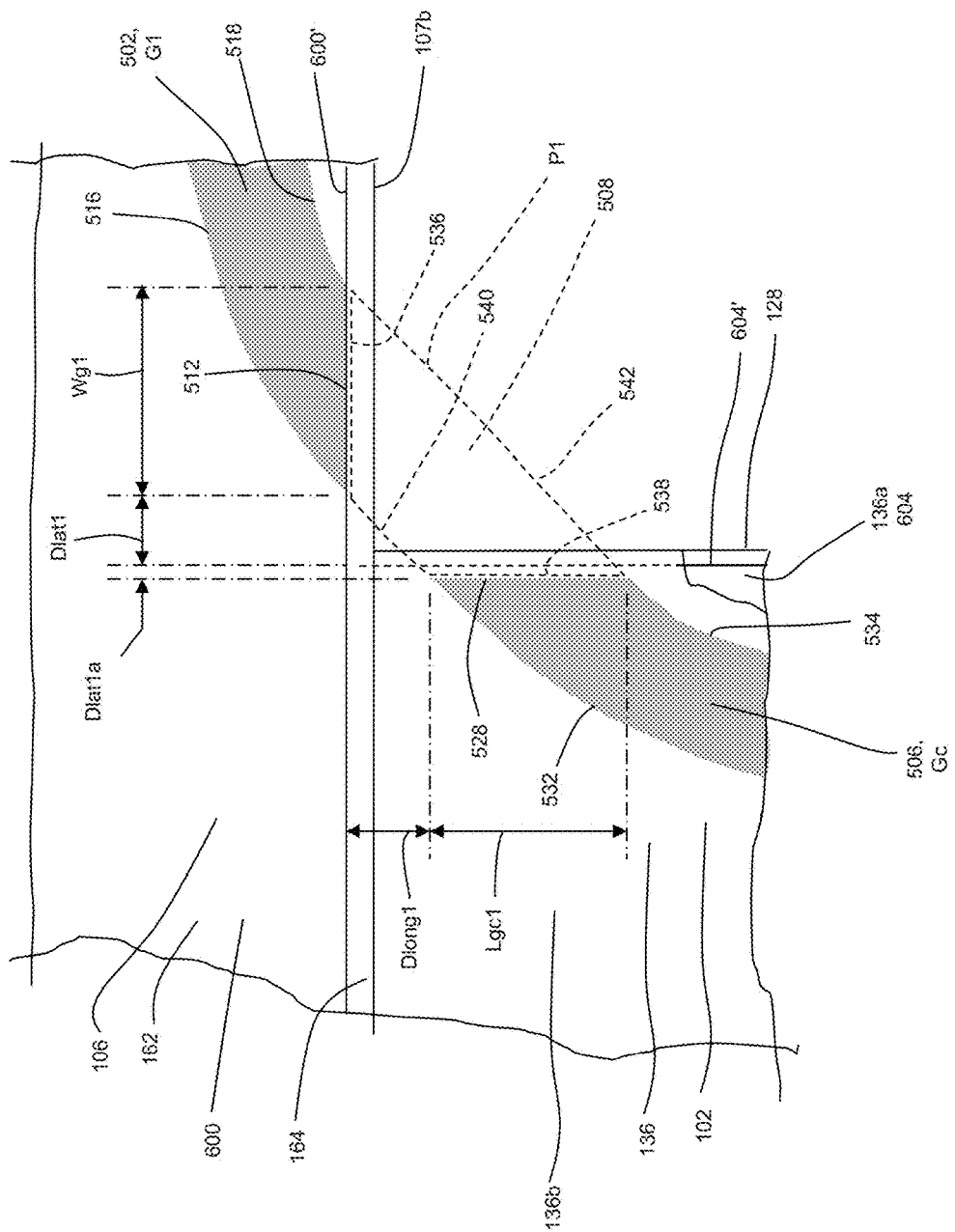
Figure 4A2

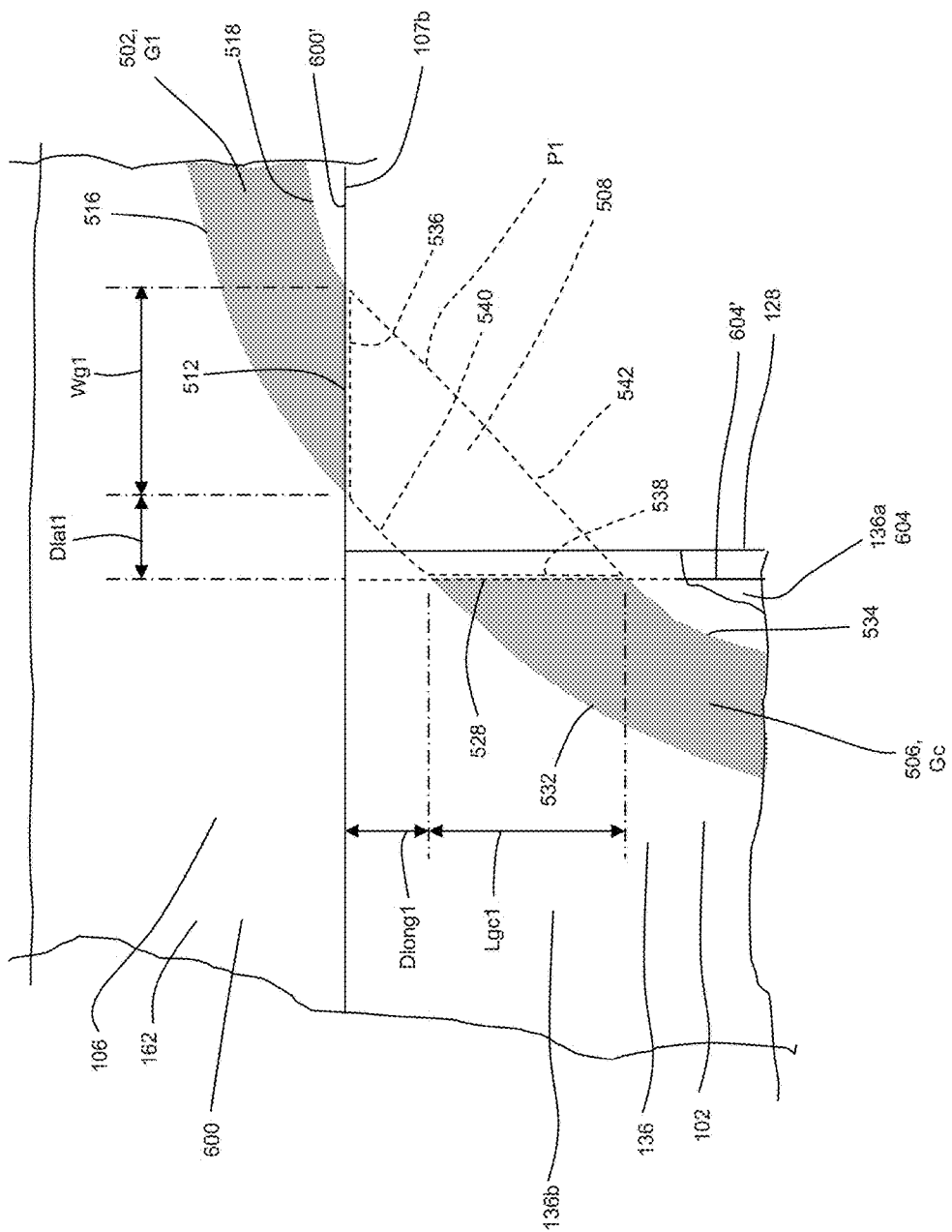

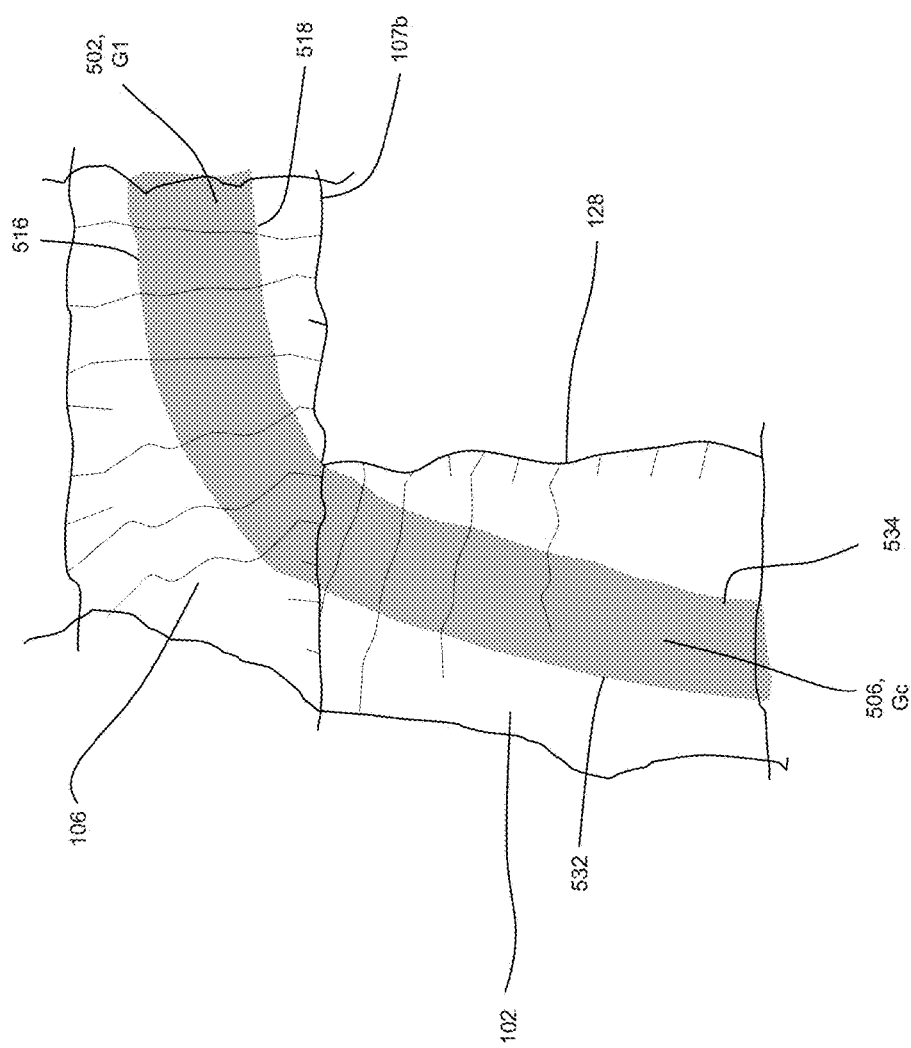
Figure 4A4

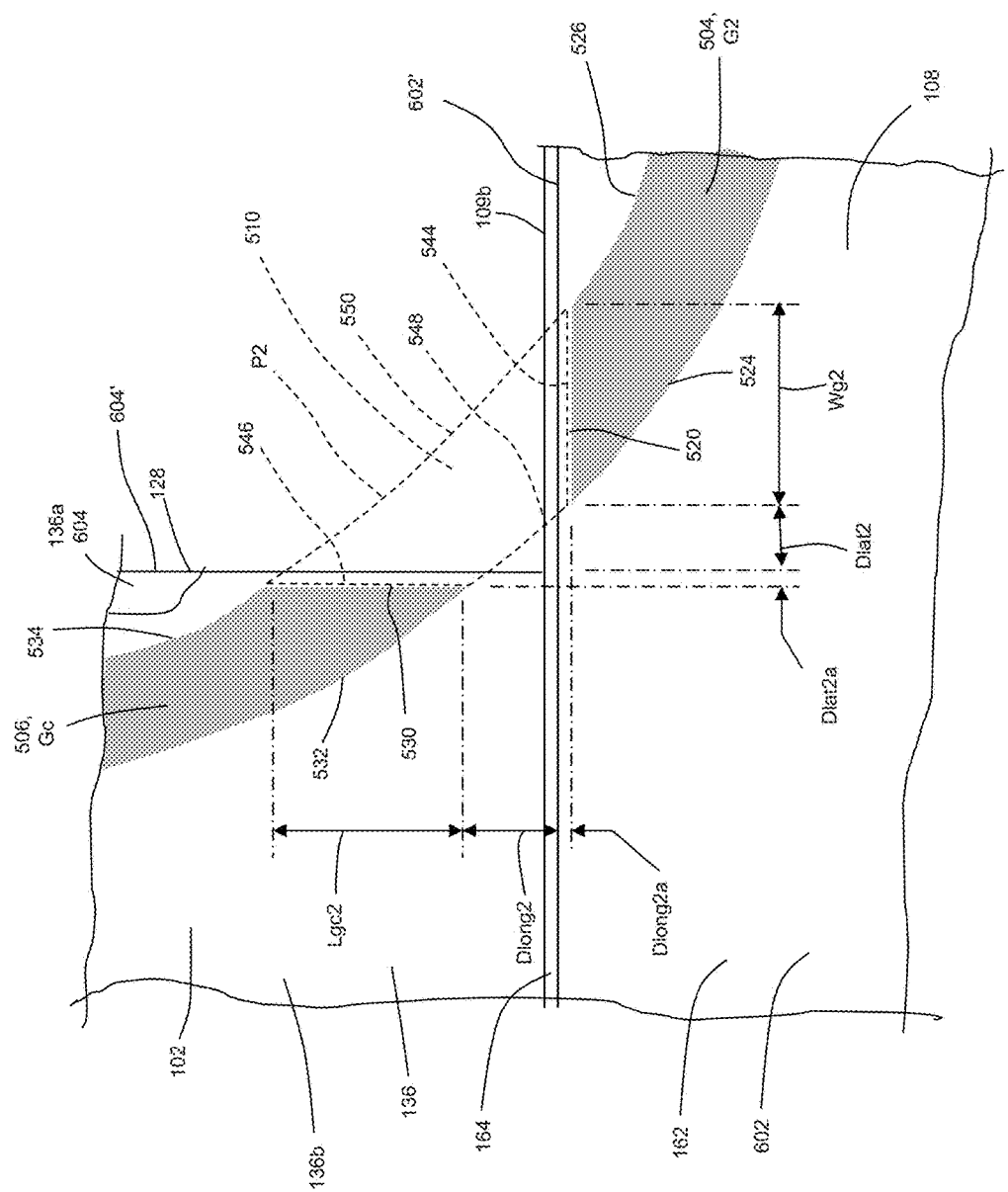
Figure 4B1

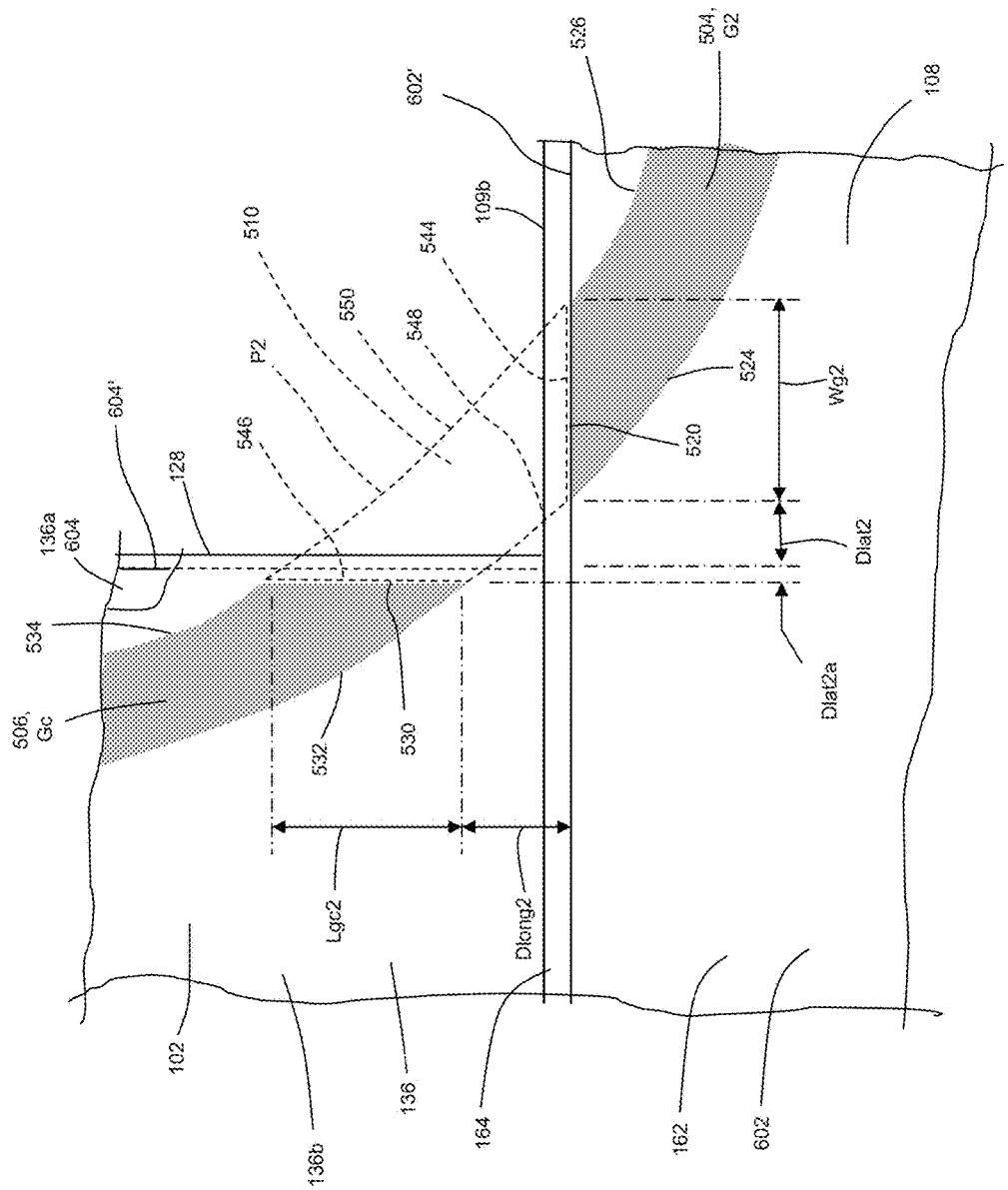
Figure 4B2

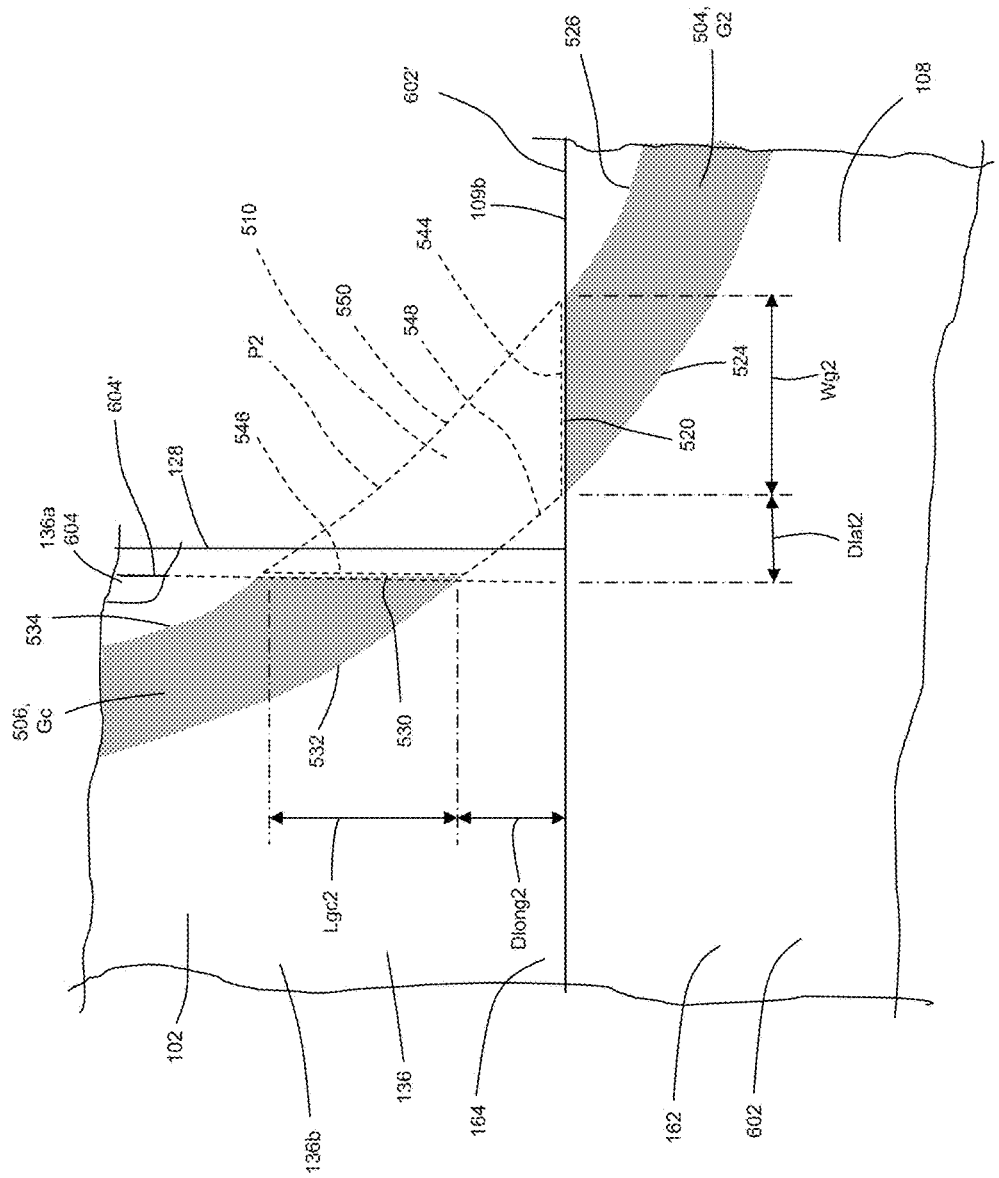
Figure 4B3

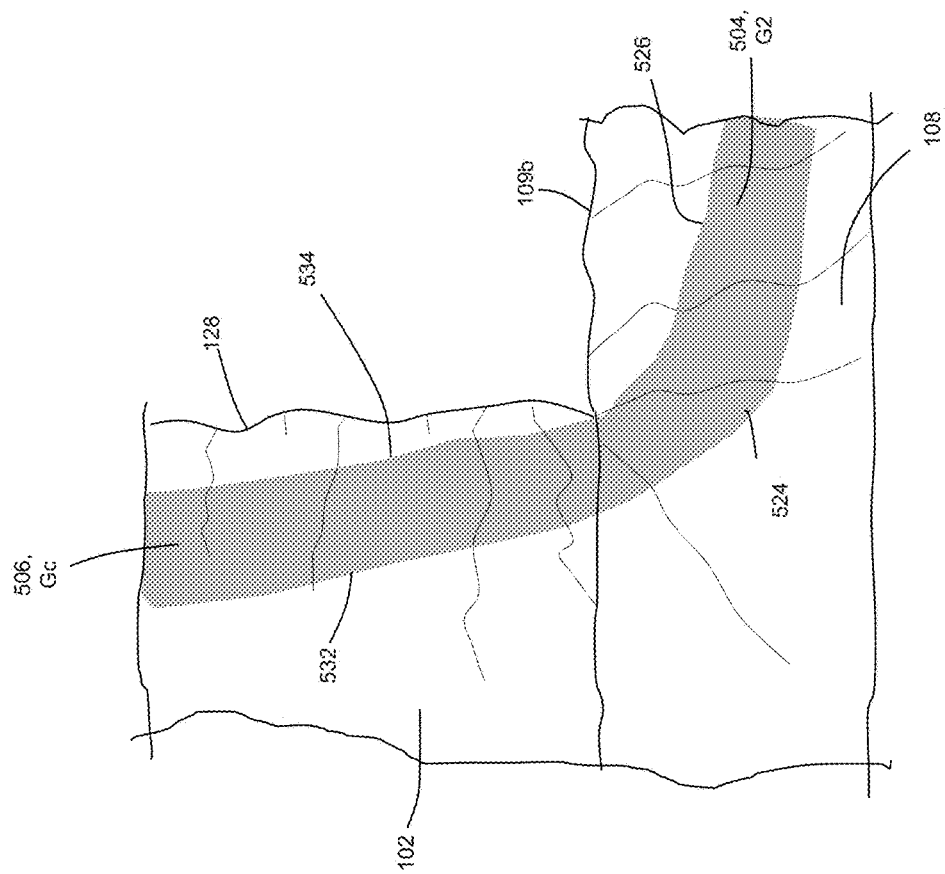
Figure 4B4

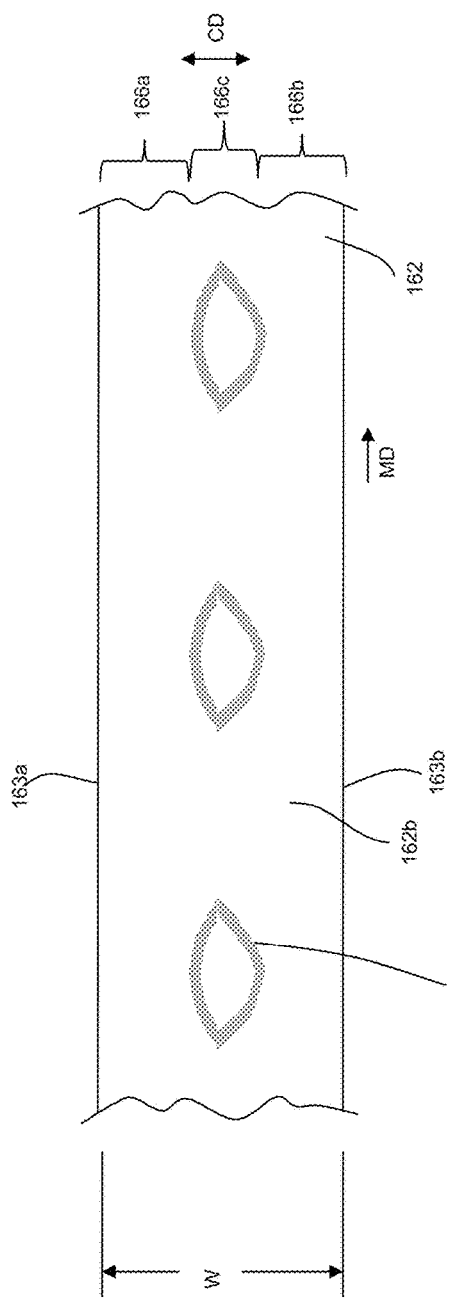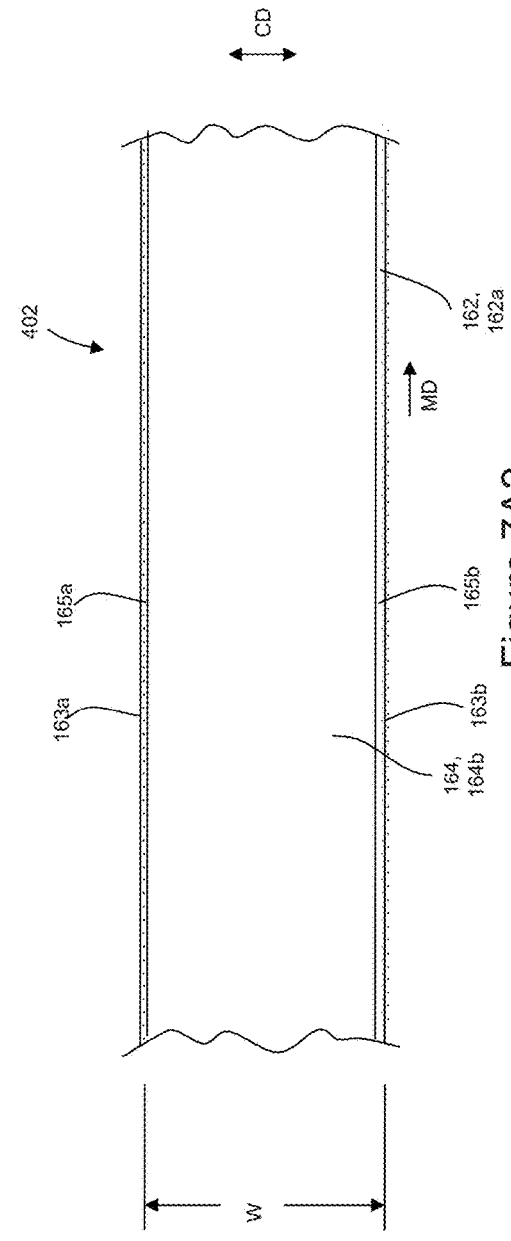

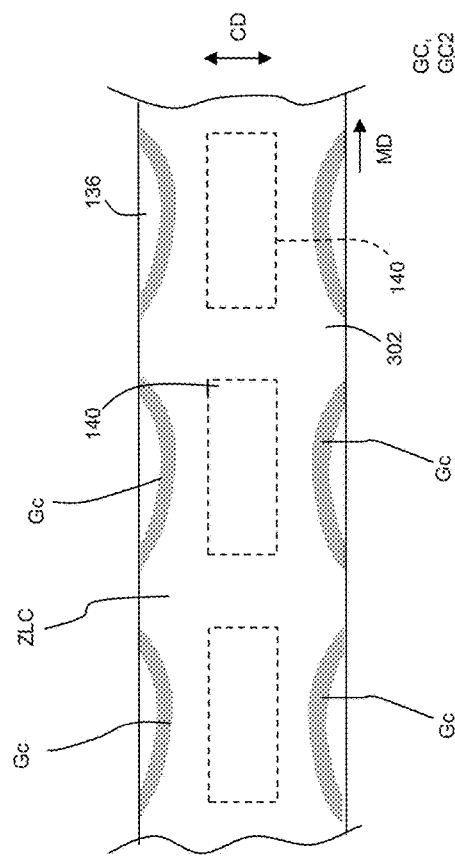
Figure 7C
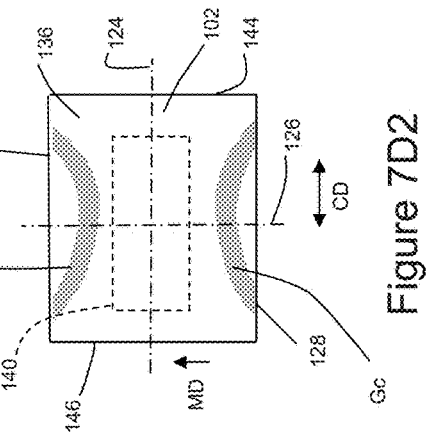
Figure 7D2
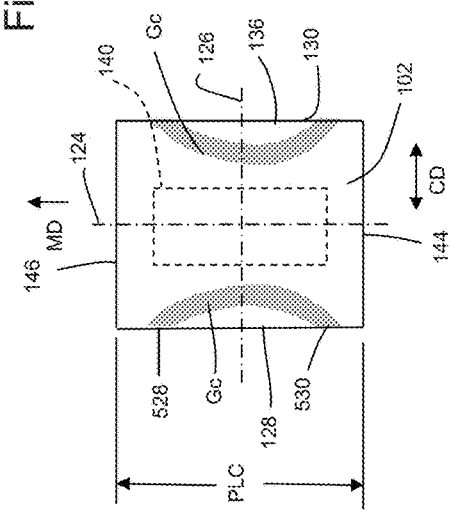
Figure 7D1

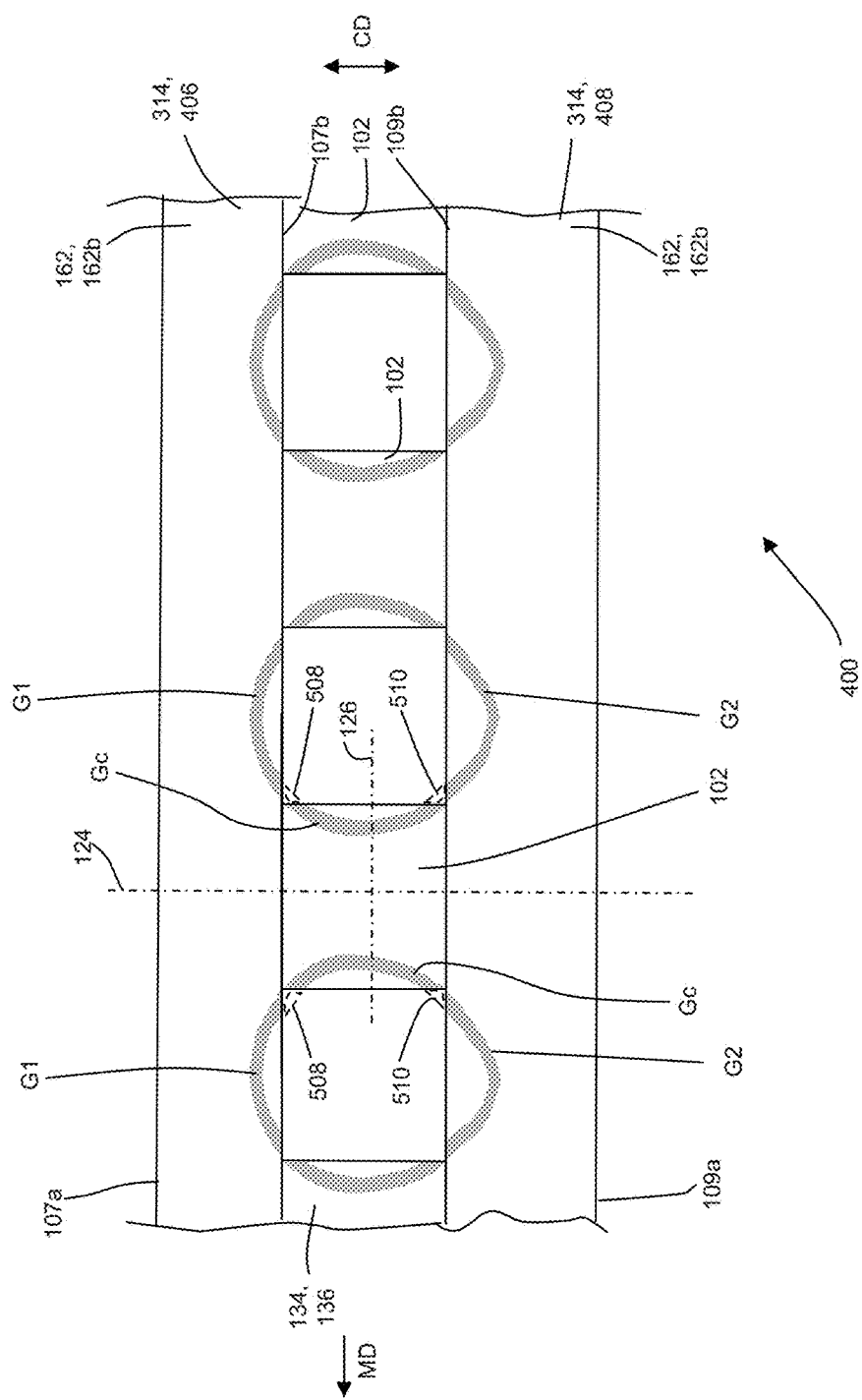
Figure 7E1

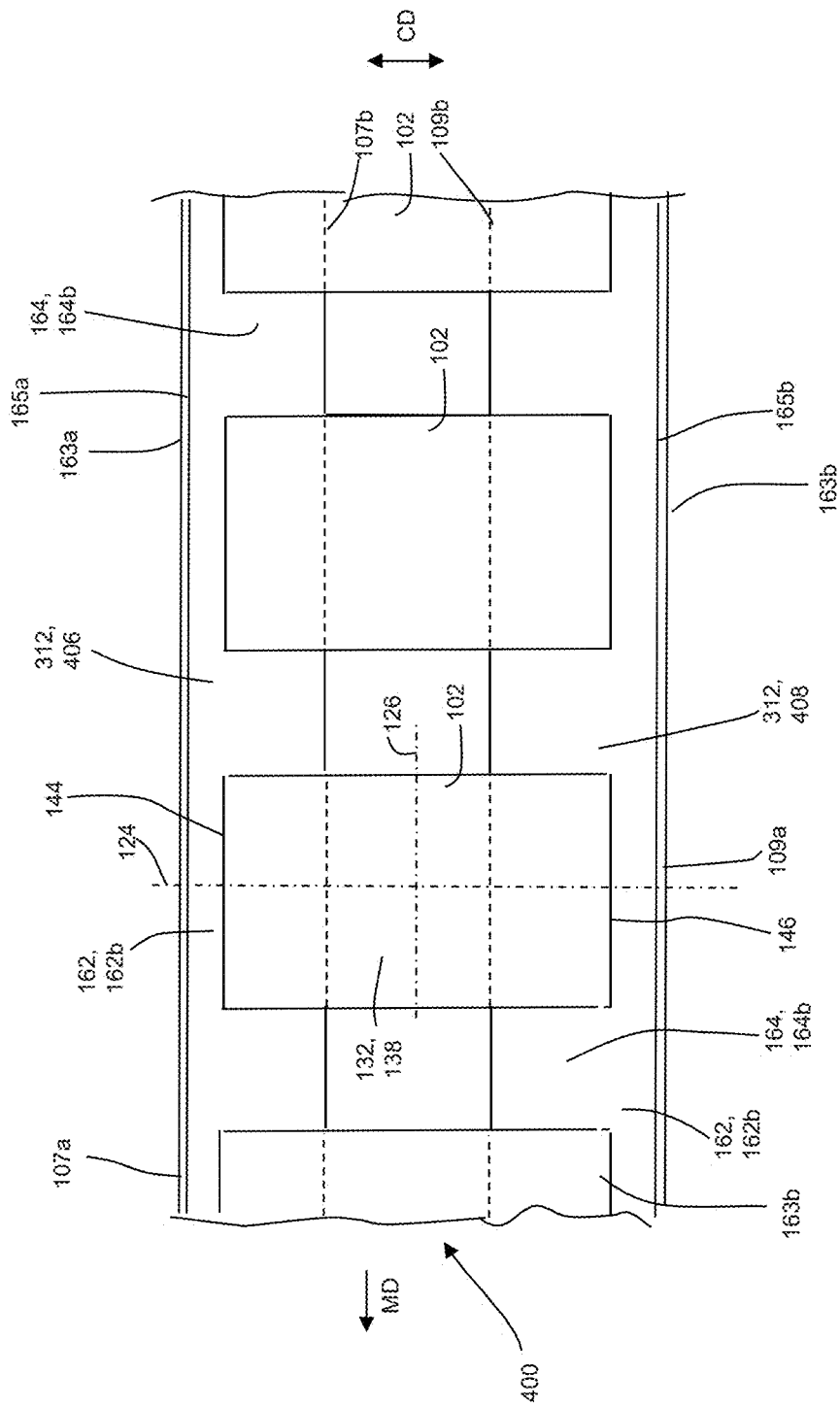
Figure 7E2

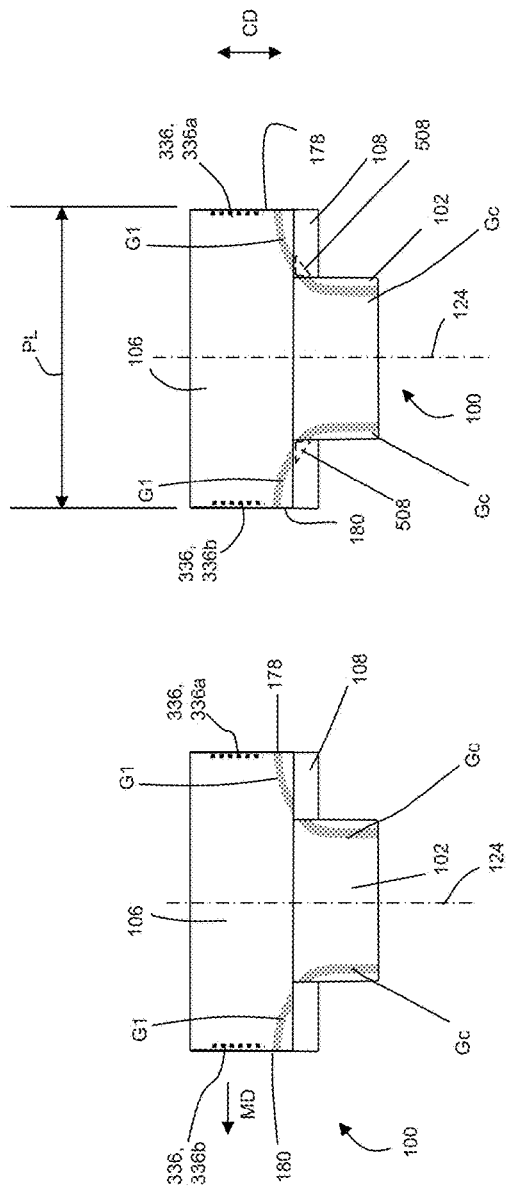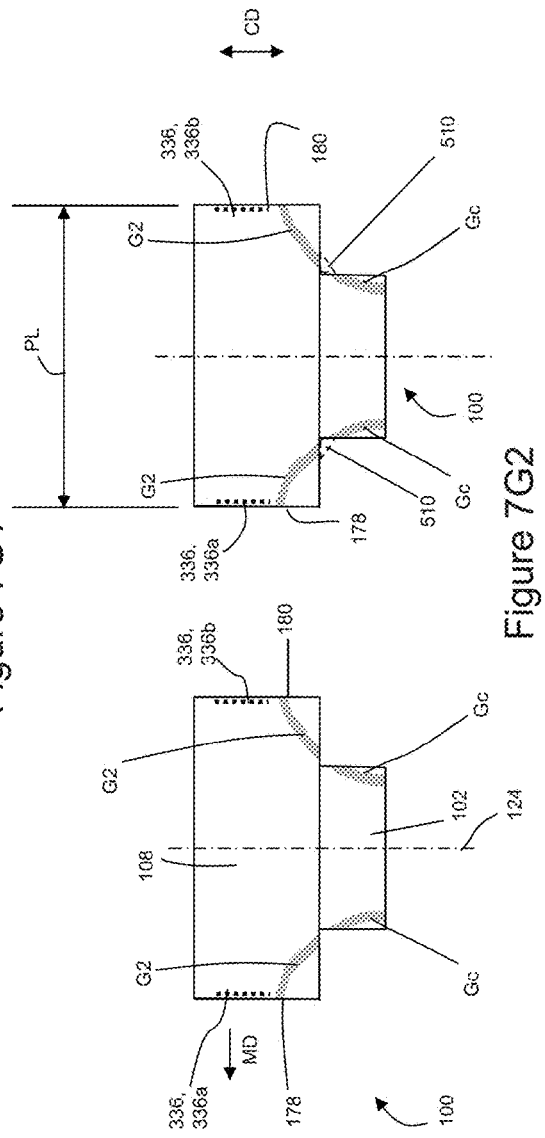
Figure 7G1
Figure 7G2

METHODS FOR MAKING DIAPER PANTS WITH A DESIGN HAVING A DISCONTINUOUS REGION BETWEEN A BELT AND CHASSIS ARRANGED TO PROVIDE A CONTIGUOUS APPEARANCE

CROSS REFERENCE TO RELATED APPLICATIONS

This application claims the benefit of U.S. Provisional Application No. 62/147,004 filed on Apr. 14, 2015, which is herein incorporated herein by reference.

FIELD OF THE INVENTION

The present disclosure relates to methods for manufacturing absorbent articles, and more particularly, to assembling diaper pants having a design including: a first region extending across a first component, a second region extending across a second component, and a discontinuous region separating the first region from the second region.

BACKGROUND OF THE INVENTION

Along an assembly line, diapers and various types of other disposable absorbent articles may be assembled by adding components to and/or otherwise modifying advancing, continuous webs of material. Webs of material and component parts used to manufacture diapers may include: backsheets, topsheets, absorbent cores, front and/or back ears, fastener components, and various types of elastic webs and components such as leg elastics, barrier leg cuff elastics, and waist elastics.

Some consumers may prefer purchasing absorbent articles, such as diapers, having various types of different graphic designs printed thereon. As such, continuous substrates of material having printed graphics may be converted into different components used to assemble the absorbent articles. During the assembly process, the substrates of material having the graphics printed thereon may be subjected to various process transformations, such as folding, bonding, trimming, and/or cutting.

In some instances, consumers may prefer diapers with graphics defining various designs and various colored areas that may be printed thereon and that may extend over the entire area, or a relatively large area, of the diaper that is visible when worn. Thus, in converting operations involving the assembly of diapers having printed graphics that extend over relatively large regions, the printed substrates may be subjected to various process transformations in areas where the printing is located. However, subjecting printed substrates to various process transformations, such as folding, cutting, bonding, and/or assemblage with other printed components in areas where the graphics are located may create challenges in performing such process transformations when attempting to maintain aesthetically pleasing final assemblies. For example, imprecise and/or inconsistent bonding, cutting, and/or folding operations performed on a substrate in an area where a printed graphic is located may act to visibly highlight such process imprecisions or inconsistencies, such as crooked bond lines, fold lines, and/or cut lines. Some diapers are configured with designs intended to extend contiguously across multiple components that are assembled during the manufacturing process. However, imprecise placement of one printed component onto another printed component may be visibly highlighted when graphics on the separate components appear disjointed and/or misaligned when the components are combined. For example, FIG. 2B1 shows an absorbent article 100 including examples of graphics G on assembled components, such as belts 106, 108 and chassis 102, that require relatively precise alignment along the intersection of the belts 106, 108 and the chassis 102 to provide the appearance of a contiguous design in the final assembly. And FIG. 2B2, particularly in areas enclosed by circles A-A and B-B, illustrates how imprecise and/or inconsistent placement of the chassis 102 relative to the belts 106, 108 during assembly results in the graphics G being disjointed. In addition, the aforementioned challenges may be exacerbated in absorbent article assembly processes operating at relatively high speed production rates.

Consequently, there remains a need to incorporate substrates and/or components into absorbent article assembly processes wherein the substrates and/or components include graphics printed and/or positioned in such a manner so as to functionally reduce noticeable visible results of imprecise and/or inconsistent manufacturing operations performed in areas where the graphics are located.

SUMMARY OF THE INVENTION

The present disclosure relates to absorbent articles and methods for assembling absorbent articles having a design including: a first region extending along a first component, a second region extending along a second component, and a discontinuous region separating the first region from the second region. In some configurations, the first region may include a first graphic printed on a first component, and the second region may include a second graphic printed on a second component. The discontinuous region helps to provide the appearance that the first and second graphics form a contiguous design while at the same time mitigating the need to precisely align the graphics on separated components to form a contiguous design.

In a method for assembling disposable diaper pants, each diaper pant comprising a chassis having a first end region and an opposing second end region separated from each other by a central region, and having a longitudinal axis and a lateral axis, the chassis comprising: a topsheet, a backsheet, and an absorbent core disposed between the topsheet and the backsheet, the method comprises the steps of: advancing a first continuous elastic laminate in a machine direction comprising an outer longitudinal edge and an inner longitudinal edge defining a width in a cross direction, the first continuous elastic laminate comprising a printed belt substrate comprising a first graphic, the first graphic extending in the machine direction and the cross direction and comprising an end edge adjacent a longitudinal edge of the printed belt substrate, the end edge having a width defined by a distance extending in the machine direction between a first side edge of the first graphic and a second side edge of the first graphic; advancing a second continuous elastic laminate comprising an outer longitudinal edge and an inner longitudinal edge; advancing a chassis in the machine direction, the chassis comprising a first side edge and a second side edge separated from the first side edge in the machine direction, the chassis comprising a printed chassis substrate comprising a second graphic comprising an end edge extending in the cross direction and adjacent a side edge of the printed chassis substrate, the end edge comprising a length defined by a distance extending between a first side edge of the second graphic and a second side edge of the second graphic; positioning the chassis onto the first continuous elastic laminate and the second continuous elastic laminate to define a discontinuous region devoid of printing and separating the first graphic from the second graphic, the discontinuous region defined by a substantially trapezoidal-shaped perimeter extending between the end edge of the first graphic and the end edge of the second graphic, defining an imaginary continuous extension of an established direction of the first graphic to the second graphic.

In another method for assembling disposable diaper pants, each diaper pant comprising a chassis having a first end region and an opposing second end region separated from each other by a central region, and having a longitudinal axis and a lateral axis, the chassis comprising: a topsheet, a backsheet, and an absorbent core disposed between the topsheet and the backsheet, the method comprises the steps of: advancing an elastic laminate in a machine direction, the elastic laminate comprising a first longitudinal edge and a second longitudinal edge, the elastic laminate further comprising a first graphic extending in the machine direction and the cross direction; cutting the elastic laminate along the machine direction and through the graphic to form a first elastic laminate comprising a first portion of the first graphic and a second elastic laminate comprising a second portion of the first graphic, wherein the first and second elastic laminates each include an inner longitudinal edge and an outer longitudinal edge, wherein the first portion of the first graphic comprises an end edge coincident with the inner longitudinal edge of the first elastic laminate, and wherein the second portion of the first graphic comprises an end edge coincident with the inner longitudinal edge of the second elastic laminate; separating the first elastic laminate in the cross direction from the second elastic laminate to define a gap between the inner longitudinal edge of the first elastic laminate and the inner longitudinal edge of the second elastic laminate; advancing a chassis in the machine direction, the chassis including a first side edge and a second side edge separated from the first side edge in the machine direction, wherein the chassis comprises a printed chassis substrate comprising a second graphic comprising a first end edge and a second end edge each extending in the cross direction and adjacent a side edge of the printed chassis substrate; positioning the chassis across the gap and onto the first elastic laminate to define a first discontinuous region devoid of printing and separating the first portion of the first graphic from the second graphic, the discontinuous region defined by a substantially trapezoidal-shaped perimeter extending between the end edge of the first portion of the first graphic and the first end edge of the second graphic.

In another form, an absorbent article comprises: a first belt comprising a first end region and a laterally opposing second end region separated from each other by a central region, the first belt comprising a printed belt substrate; a second belt comprising a first end region and a laterally opposing second end region separated from each other by a central region, and wherein the first end region of the first belt is connected with the first end region of the second belt, and wherein the second end region of the first belt is connected with the second end region of the second belt; a chassis comprising, a topsheet, a backsheet, and an absorbent core positioned between the topsheet and the backsheet, the chassis further comprising a first waist region and a second waist region separated from each other by a crotch region, wherein the first waist region is connected with the central region of the first belt and the second waist region is connected with the central region of the second belt, the chassis further comprising a printed chassis substrate; a design extending across a portion of the first belt and a portion of the chassis, the design comprising: a first region comprising a first graphic printed directly on the printed belt substrate of the first belt, the first graphic comprising an end edge having a width defined by a distance extending laterally between a first side edge of the first graphic and a second side edge of the first graphic, wherein the first side edge of the first graphic is laterally outboard from the printed chassis substrate and laterally inboard of the second side edge of the first graphic; a second region comprising a second graphic printed directly on printed chassis substrate, the second graphic comprising an end edge having a length defined by a distance extending longitudinally between a first side edge of the second graphic and a second side edge of the second graphic, the first side edge of the second graphic longitudinally inboard from the printed belt substrate and longitudinally outboard of the second side edge of the second graphic; a discontinuous region devoid of printing and separating the first region from the second region, the discontinuous region defined by a substantially trapezoidal-shaped perimeter extending between the end edge of the first graphic and the end edge of the second graphic.

BRIEF DESCRIPTION OF THE DRAWINGS

FIG. 2A is a partially cut away plan view of the diaper pant shown in FIGS. 1A and 1B in a flat, uncontracted state.

FIG. 2B1 is a plan view of the diaper pant shown in a flat, uncontracted state and including graphics on the belts and chassis that require relatively precise alignment along the intersection of the belts and the chassis to provide the appearance of a contiguous design.

FIG. 2B2 is a view of the diaper of FIG. 2B1 illustrating the resulting disjointed graphics caused by imprecise and/or inconsistent placement of the chassis relative to the belts during assembly.

FIG. 3A is a cross-sectional view of the diaper pant of FIG. 2A taken along line 3A-3A.

FIG. 3B is a cross-sectional view of the diaper pant of FIG. 2A taken along line 3B-3B.

FIG. 4A1 is a detailed view of an embodiment of a discontinuous region of the design shown in FIG. 2B that is devoid of printing between the first belt and the chassis.

FIG. 4A2 is a detailed view of an embodiment of a discontinuous region of the design shown in FIG. 2B that is devoid of printing between the first belt and the chassis.

FIG. 4A3 is a detailed view of an embodiment of a discontinuous region of the design shown in FIG. 2B that is devoid of printing between the first belt and the chassis.

FIG. 4A4 is a detailed view of the intersection of the chassis and first belt once tension is removed from elastic material in the first belt and/or chassis and has contracted.

FIG. 4B1 is a detailed view of an embodiment of a discontinuous region of the design shown in FIG. 2B that is devoid of printing between the second belt and the chassis.

FIG. 4B2 is a detailed view of an embodiment of a discontinuous region of the design shown in FIG. 2B that is devoid of printing between the second belt and the chassis.

FIG. 4B3 is a detailed view of an embodiment of a discontinuous region of the design shown in FIG. 2B that is devoid of printing between the second belt and the chassis.

FIG. 4B4 is a detailed view of the intersection of the chassis and second belt once tension is removed from elastic material in the second belt and/or chassis and has contracted.

FIG. 7A1 is a view of a continuous length of an advancing first substrate from FIG. 6 taken along line A1-A1.

FIG. 7A2 is a view of a continuous length of an advancing elastic laminate from FIG. 6 taken along line A2-A2.

FIG. 7C is a view of a continuous length of chassis assemblies from FIG. 6 taken along line C-C.

FIG. 7D1 is a view of a discrete chassis from FIG. 6 taken along line D1-D1.

FIG. 7D2 is a view of a discrete chassis from FIG. 6 taken along line D2-D2.

FIG. 7E1 is a view of multiple discrete chassis spaced from each other along the machine direction MD and connected with each other by the first and second elastic belt laminates from FIG. 6 taken along line E1-E1.

FIG. 7E2 is a view of multiple discrete chassis spaced from each other along the machine direction MD and connected with each other by the first and second elastic belt laminates from FIG. 6 taken along line E2-E2.

FIG. 7G1 is a view of two discrete absorbent articles advancing the machine direction MD from FIG. 6 taken along line G-G.

FIG. 7G2 is a rear view of the two discrete absorbent articles from FIG. 7G1.

DETAILED DESCRIPTION OF THE INVENTION

Figure 1A:
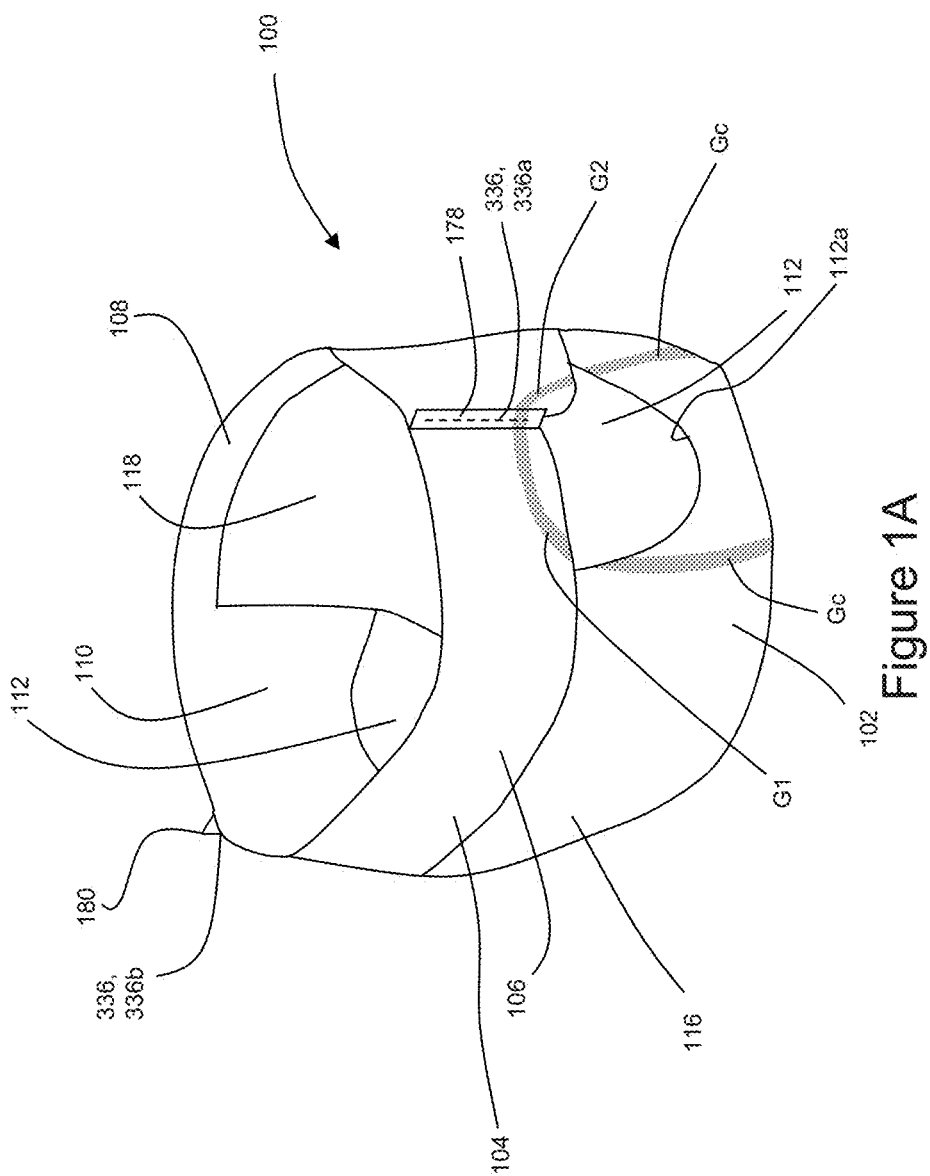
FIG. 1A is a front perspective view of a diaper pant.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

As used herein, the term "graphic" refers to printed areas of substrates. Graphics may include a color difference or transition of one or more colors and may define images or designs that are constituted by a figure (for example, a line(s), a symbol or character), or the like. A graphic may include an aesthetic image or design that can provide certain benefit(s) when viewed. A graphic may be in the form of a photographic image. A graphic may also be in the form of a 1-dimensional (1-D) or 2-dimensional (2-D) bar code or a quick response (QR) bar code. A graphic design is determined by, for example, the color(s) used in the graphic (individual pure ink or spot colors as well as built process colors), the sizes of the entire graphic (or components of the graphic), the positions of the graphic (or components of the graphic), the movements of the graphic (or components of the graphic), the geometrical shapes of the graphic (or components of the graphics), the number of colors in the graphic, the variations of the color combinations in the graphic, the number of graphics printed, the disappearance of color(s) in the graphic, and the contents of text messages in the graphic.

It is to be appreciated that all graphics discussed herein may be in various different forms, shapes, and/or sizes than those depicted herein. It is also to be appreciated that the graphics described herein may be configured to be different graphics, standard graphics, custom graphics, and/or personalized graphics. "Different in terms of graphic design" means that graphics are intended to be different when viewed by users or consumers with normal attentions. Thus, two graphics having a graphic difference(s) which are unintentionally caused due to a problem(s) or an error(s) in a manufacture process, for example, are not different from each other in terms of graphic design. "Standard" or "standardized" refers to graphics, products, and/or articles that have the same aesthetic appearance without intending to be different from each other. The term "custom" or "customized" refers to graphics, products, and/or articles that are changed to suit a small demographic, region, purchaser, customer, or the like. Custom graphics may be selected from a set of graphics. For example, custom graphics may include animal depictions selected from groups of animals, such as farm animals, sea creatures, birds, and the like. In other examples, custom graphics may include nursery rhymes and the like. In one scenario, custom products or articles may be created by a purchaser of such products or articles wherein the purchaser selects graphics for the articles or products from a set of graphics offered by a manufacturer of such articles or products. Custom graphics may also include "personalized" graphics, which may be graphics created for a particular purchaser. For example, personalized graphics may include a person's name alone or in combination with a design.

In addition, all graphics discussed herein may be printed so as to fade from a high intensity zone to a low intensity zone such as disclosed in U.S. Patent Application Nos. 62/093,620; 62/093,438; 62/093,452; 62/093,516; and 62/093,604, filed on Dec. 18, 2014, all of which are incorporated herein by reference. As used herein, the term "fade" means a visible gradual change in color hue, brightness, lightness, chroma, and/or saturation, for example, when a graphic fades from an area having a relatively high print density to an area having a relatively low print density. Further, the graphics herein may also be configured to change, appear, and/or disappear during usage.

"Longitudinal" means a direction running substantially perpendicular from a waist edge to a longitudinally opposing waist edge of an absorbent article when the article is in a flat out, uncontracted state, or from a waist edge to the bottom of the crotch, i.e., the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e., in an XY plane) and whose thickness (in a Z direction) is relatively small (i.e., 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed).

The present disclosure relates to absorbent articles and methods for assembling absorbent articles having a design including: a first region extending across a first component, a second region extending across a second component, and a discontinuous region separating the first region from the second region. In some configurations, the first region may include a first graphic printed on a first component. And the second region may include a second graphic printed on a second component. During the assembly process, the first and second components are combined to form a discontinuous region devoid of printing and separating the first region from the second region. As discussed in more detail below, the discontinuous region may be defined by a substantially trapezoidal-shaped perimeter extending between an end edge of the first graphic and an end edge of the second graphic that defines an imaginary continuous extension of an established direction of the first graphic to the second graphic. Thus, the discontinuous region helps to provide the appearance that the first and second graphics form a contiguous design while at the same time mitigating the need to precisely align the graphics on separated components to form a contiguous design. As such, substrates and/or components to be incorporated into manufactured absorbent articles herein include graphics that are positioned and/or printed in such a manner so as to functionally reduce noticeable visible results of imprecise and/or inconsistent manufacturing operations performed in areas where the graphics are located.

As previously mentioned, the processes and apparatuses discussed herein may be used in the manufacture of different types of absorbent articles. To help provide additional context to the subsequent discussion of the process embodiments, the following provides a general description of absorbent articles in the form of diaper pants that include belt substrates that may be assembled in accordance with the methods and apparatuses disclosed herein.

Figure 1B:
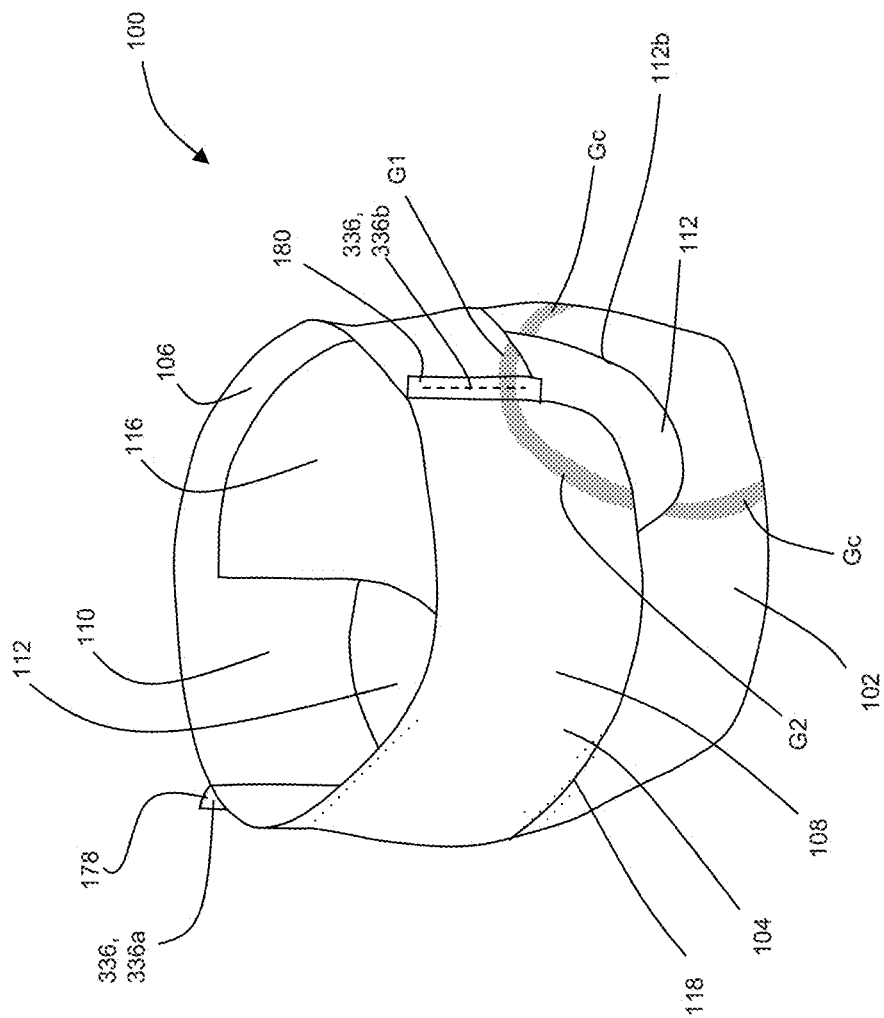
FIG. 1B is a rear perspective view of a diaper pant.
Figure 2B:
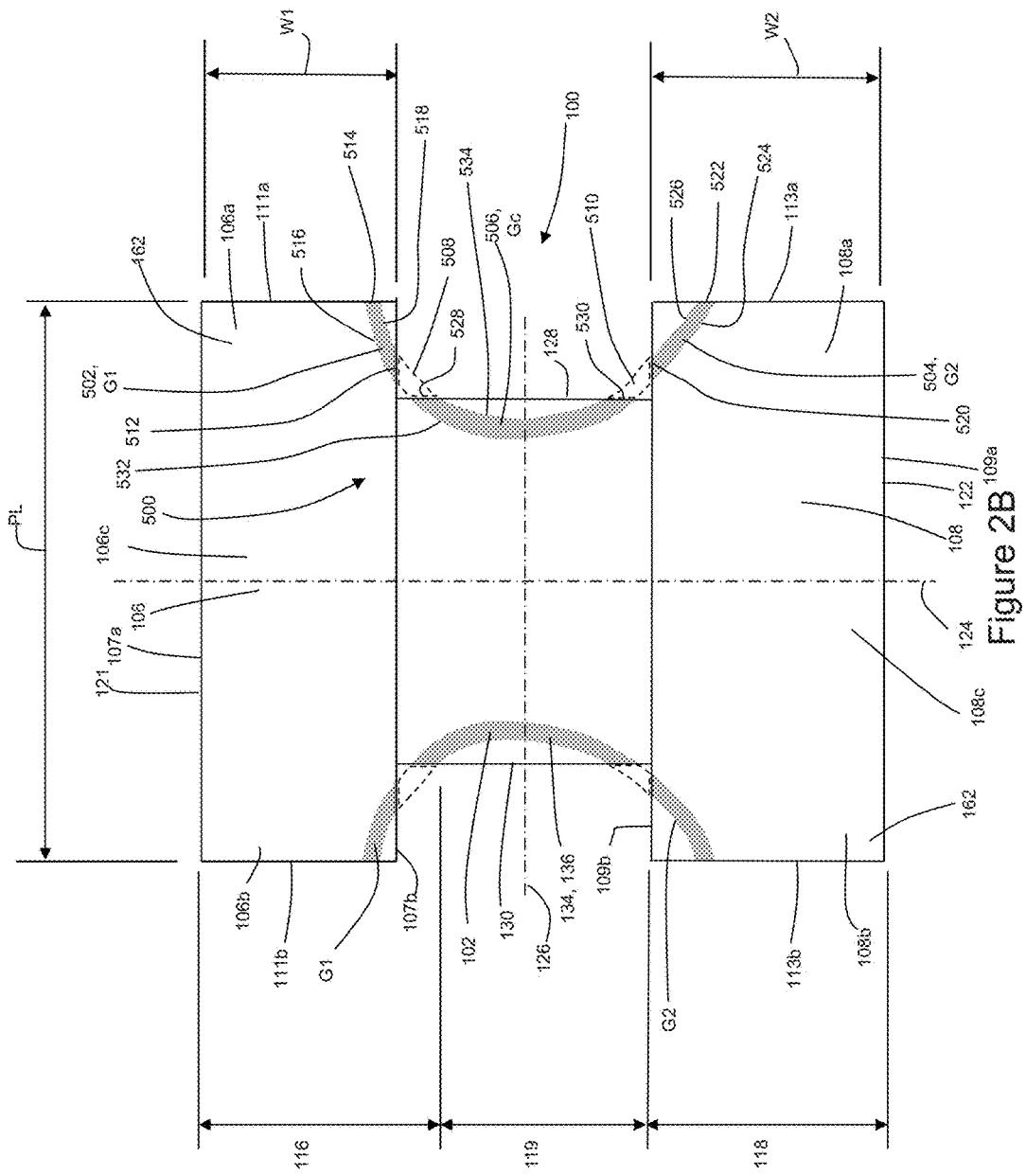
FIG. 2B is a plan view of the diaper pant shown in FIGS. 1A and 1B in a flat, uncontracted state and including a design extending across a first belt, a second belt, and a chassis.

FIGS. 1A, 1B, 2A, and 2B show an example of a diaper pant 100 that may be assembled in accordance with the apparatuses and methods disclosed herein. In particular, FIGS. 1A and 1B show perspective views of a diaper pant 100 in a pre-fastened configuration, and FIGS. 2A and 2B show plan views of the diaper pant 100 with the portion of the diaper that faces away from a wearer oriented toward the viewer. The diaper pant 100 includes a chassis 102 and a ring-like elastic belt 104. As discussed below in more detail, a first elastic belt 106 and a second elastic belt 108 are bonded together to form the ring-like elastic belt 104.

With continued reference to FIGS. 2A and 2B, the diaper pant 100 and the chassis 102 each include a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the diaper 100 and chassis 102 of FIGS. 2A and 2B are shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1A, 1B, 2A, and 2B, the diaper pant 100 may include an inner, body facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100 may also include other features, such as leg elastics and/or leg cuffs to enhance the fit around the legs of the wearer.

As shown in FIGS. 2A and 2B, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 are located longitudinally inward from the laterally extending front waist edge 121 in the front waist region 116 and the laterally extending back waist edge 122 in the back waist region 118. When the diaper pant 100 is worn on the lower torso of a wearer, the front waist edge 121 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, the user of the diaper 100, including a chassis 102 having a particular size before extension, to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured in part from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper pant 100 may also include an absorbent assembly 140 that is joined to the chassis 102. As shown in FIG. 2A, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; and U.S. Patent Publication No. 2009/0312730 A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIGS. 1A and 1B. The ring-like elastic belt may be formed by joining a first elastic belt to a second elastic belt with a permanent side seam or with an openable and reclosable fastening system disposed at or adjacent the laterally opposing sides of the belts.

As previously mentioned, the ring-like elastic belt 104 may be defined by a first elastic belt 106 connected with a second elastic belt 108. As shown in FIGS. 2A and 2B, the first elastic belt 106 extends between a first longitudinal side edge 111a and a second longitudinal side edge 111b and defines first and second opposing end regions 106a, 106b and a central region 106c. And the second elastic 108 belt extends between a first longitudinal side edge 113a and a second longitudinal side edge 113b and defines first and second opposing end regions 108a, 108b and a central region 108c. The distance between the first longitudinal side edge 111a and the second longitudinal side edge 111b defines the pitch length, PL, of the first elastic belt 106, and the distance between the first longitudinal side edge 113a and the second longitudinal side edge 113b defines the pitch length, PL, of the second elastic belt 108. The central region 106c of the first elastic belt is connected with the first waist region 116 of the chassis 102, and the central region 108c of the second elastic belt 108 is connected with the second waist region 116 of the chassis 102. As shown in FIGS. 1A and 1B, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

It is to be appreciated that the first and second elastic belts may define various pitch lengths PL. For example, in some embodiments, the pitch lengths PL of the first and/or second elastic belts may be about 300 mm to about 1100 mm.

As shown in FIGS. 2A, 3A, and 3B, the first elastic belt 106 also defines an outer laterally extending edge 107a and an inner laterally extending edge 107b, and the second elastic belt 108 defines an outer laterally extending edge 109a and an inner laterally extending edge 109b. As such, a perimeter edge 112a of one leg opening may be defined by portions of the inner laterally extending edge 107b of the first elastic belt 106, the inner laterally extending edge 109b of the second elastic belt 108, and the first longitudinal or right side edge 128 of the chassis 102. And a perimeter edge 112b of the other leg opening may be defined by portions of the inner laterally extending edge 107b, the inner laterally extending edge 109b, and the second longitudinal or left side edge 130 of the chassis 102. The outer laterally extending edges 107a, 109a may also define the front waist edge 121 and the laterally extending back waist edge 122 of the diaper pant 100. The first elastic belt and the second elastic belt may also each include an outer, garment facing layer 162 and an inner, wearer facing layer 164. Also, as shown in FIG. 2B, the distance between the outer laterally extending edge 107a and the inner laterally extending edge 107b may define a width, W1, of the first belt 106. And the distance between the outer laterally extending edge 109a and the inner laterally extending edge 109b may define a width, W2, of the second belt 108, wherein W2 may be greater than W1. It is to be appreciated that in some configurations, W1 may be equal to or greater than W2. In some embodiments, the widths W1 and/or W2 may from about 120 mm to about 300 mm.

It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer substrate layer 162 and the inner substrate layer 164. The belt elastic material may include one or more elements such as strands, ribbons, films, or panels extending along the lengths of the elastic belts. As shown in FIGS. 2A, 3A, and 3B, the belt elastic material may include a plurality of elastic strands 168 which may be referred to herein as outer, waist elastics 170 and inner, waist elastics 172. Elastic strands 168, such as the outer waist elastics 170, may continuously extend laterally between the first and second opposing end regions 106a, 106b of the first elastic belt 106 and between the first and second opposing end regions 108a, 108b of the second elastic belt 108. In some embodiments, some elastic strands 168, such as the inner waist elastics 172, may be configured with discontinuities in areas, such as for example, where the first and second elastic belts 106, 108 overlap the absorbent assembly 140. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2A. The belt elastic material may be joined to the outer and/or inner layers continuously or intermittently along the interface between the belt elastic material and the inner and/or outer belt layers.

In some configurations, the first elastic belt 106 and/or second elastic belt 108 may define curved contours. For example, the inner lateral edges 107b, 109b of the first and/or second elastic belts 106, 108 may include non-linear or curved portions in the first and second opposing end regions. Such curved contours may help define desired shapes to leg opening 112, such as for example, relatively rounded leg openings. In addition to having curved contours, the elastic belts 106, 108 may include elastic strands 168, 172 that extend along non-linear or curved paths that may correspond with the curved contours of the inner lateral edges 107b, 109b.

As previously mentioned, the diaper pant 100 may include a design including: a first region extending across a first component, a second region extending across a second component, and a discontinuous region separating the first region from the second region. In some configurations, the first region may include a first graphic printed on a first component. And the second region may include a second graphic printed on a second component. During the assembly process, the first and second components are combined to form a discontinuous region devoid of printing and separating the first region from the second region. Thus, the graphics on the diaper components may be printed and/or positioned in such a manner so as to reduce noticeable visible results of imprecise and/or inconsistent assembly operations performed in areas where the graphics are located. As such, discontinuous regions may be positioned in locations that are subject to combining transformations during the assembly process, such as locations adjacent intersections between inner belt edges and chassis side edges.

It is to be appreciated that the graphics described herein may be printed in various ways and may be printed by various types of printing accessories, such as ink jet, flexography, and/or gravure printing processes. Ink-jet printing is a non-impact dot-matrix printing technology in which droplets of ink are jetted from a small aperture directly to a specified position on a media to create a graphic. Two examples of inkjet technologies include thermal bubble or bubble jet and piezoelectric. Thermal bubble uses heat to apply to the ink, while piezoelectric uses a crystal and an electric charge to apply the ink. In some configurations, the printing stations may include a corona treater, which may be positioned upstream of the printer. The corona treater may be configured to increase the surface energy of the surface of the substrate to be printed. In some configurations, the printing stations may also include an ink curing apparatus. In some configurations, the ink curing apparatus may be in the form of an ultraviolet (UV) light source that may include one or more ultraviolet (UV) lamps, which may be positioned downstream of the printer to help cure inks deposited onto the substrate from the printer to form the graphics. In some configurations, the ink curing apparatus may also include an infrared (IR) dryer light source that may include one or more infrared (IR) lamps, which may be positioned downstream of the printer to help dry water-based or solvent-based inks deposited onto the substrate to form the graphics. In some configurations, the ink curing apparatus may include an electron beam (EB or e-beam) generator that may include one or more e-beam electrodes, which may be positioned downstream of the printer to help cure inks deposited onto the substrate from the printer to form the graphics. In some configurations, graphics may be created using pigments or dyes embedded in another fluid such as a glue or lotion, such as disclosed in U.S. Patent Publication No. 2014/0148773 A1.

Figure 5A:
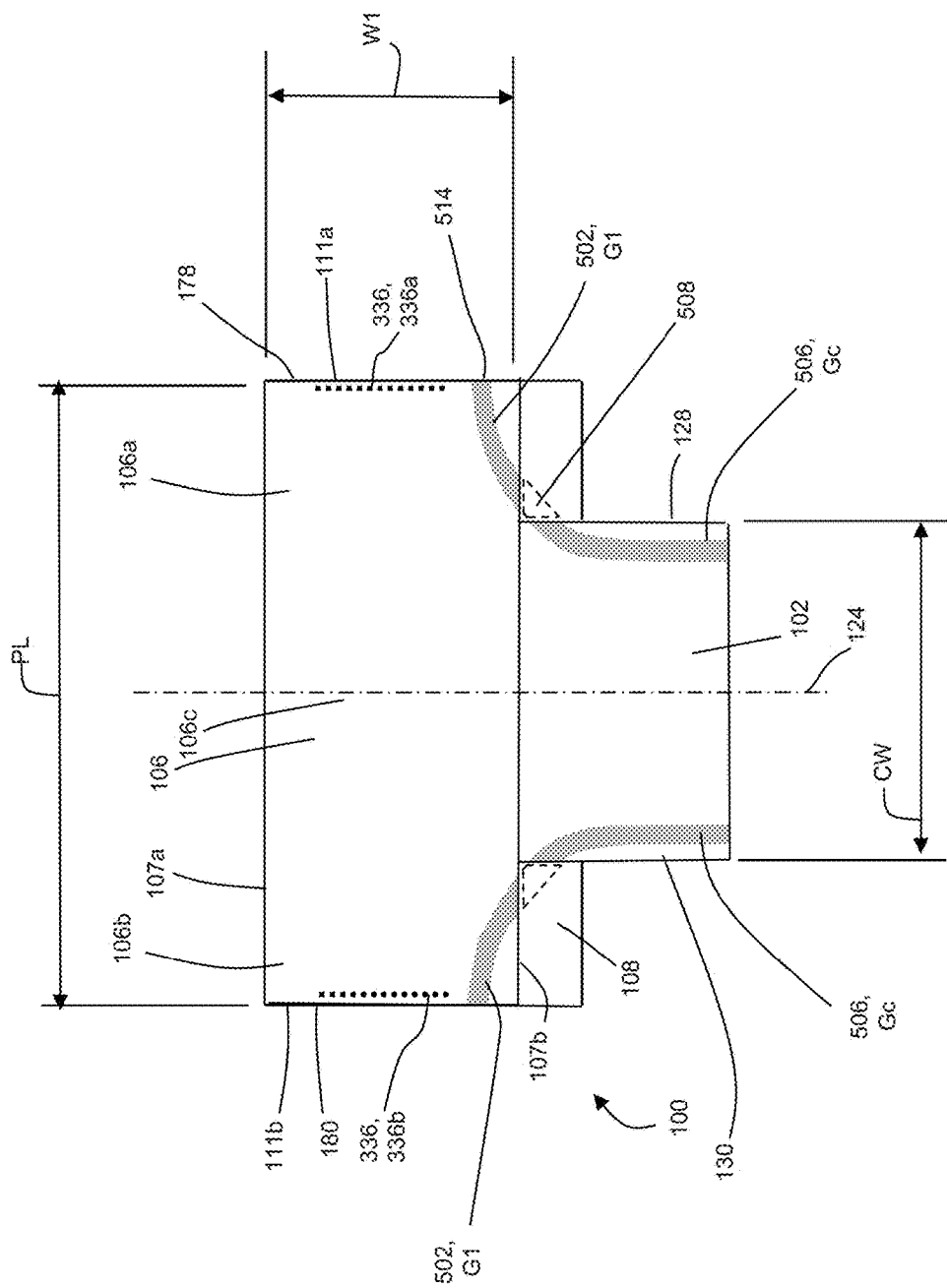
FIG. 5A is a front view of an absorbent article having belt and chassis graphics aligned to define a design having discontinuous regions.
Figure 5B:
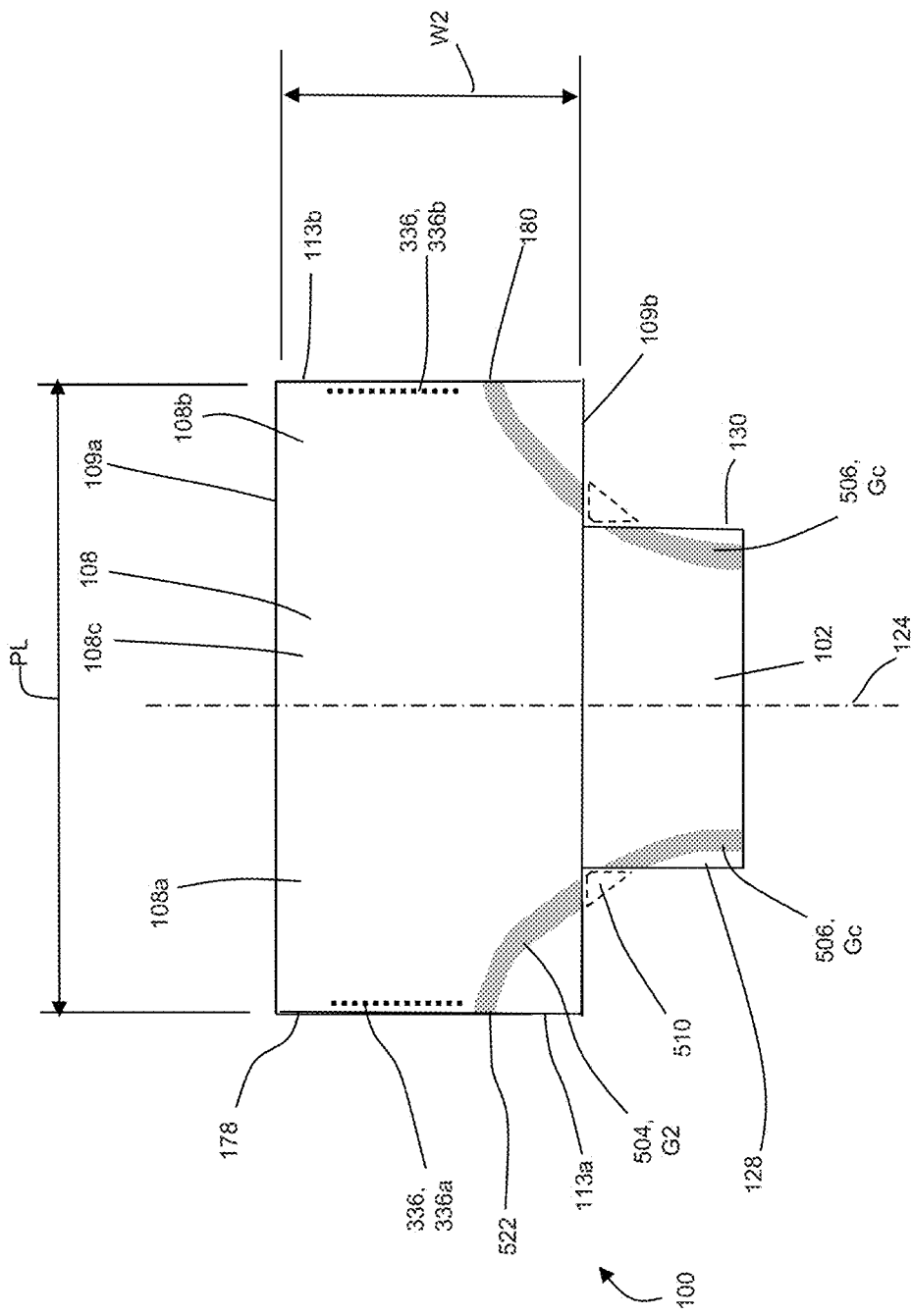
FIG. 5B is a rear view of the absorbent article from FIG. 5A.

FIGS. 2B, 5A, and 5B show an example diaper pant 100 including a design 500 extending across the first elastic belt 106, the second elastic belt 108, and the chassis 102. As shown in FIG. 2B, the design 500 may include a first region 502, a second region 504, a third region 506, a first discontinuous region 508, and a second discontinuous region 510. More particularly, the first region 502 comprises a first graphic G1 printed directly on the first elastic belt 106; the second region 504 comprises a second graphic G2 printed directly on the second elastic belt 108; and the third region 506 comprises a chassis graphic Gc printed on the chassis 102. In turn, the first discontinuous region 508 separates the first region 502 from the third region 506 and is devoid of printing. And the second discontinuous region 510 separates the second region 504 from the third region 506 and is devoid of printing. As discussed above, the first belt 106 and the second belt 108 may include one or more substrate layers, such as the outer substrate layer 162 and the inner substrate layer 164. And it is to be appreciated that the first graphic G1 and/or the second graphic G1 may be printed on any of the substrate layers 162, 164, and in turn, is referred to herein as a printed belt substrates 600, 602. Similarly, as discussed above, the chassis 102 may include one or more substrate layers, such as the backsheet 136 and the topsheet 138. In addition, the backsheet 136 and/or topsheet 138 may include one or more substrate layers. For example, as discussed above, the backsheet 136 may include a nonwoven layer substrate and a film layer substrate. And it is to be appreciated that the chassis 102 may be printed on any of the substrate layers of the chassis 102, and in turn, is referred to herein as a printed chassis substrate 604.

As shown in FIGS. 2B, 4A1, and 5A, the first graphic G1 defines a general stripe shape and extends from a first end edge 512 to a second end edge 514, and has a width Wg1 at the first end edge 512 defined by a distance extending laterally between a first side edge 516 and a second side edge 518 of the first graphic G1. In addition, the first side edge 516 of the first graphic G1 is laterally outboard relative the longitudinal axis 124 from a first side edge 604' of the printed chassis substrate 604 and laterally inboard relative the longitudinal axis 124 of the second side edge 518 of the first graphic G1. The first end edge 512 of the first graphic G1 extends between the first side edge 516 and the second side edge 518 adjacent an inner lateral end edge 600' of the printed belt substrate 600 of the first belt 106, and the second end edge 514 of the first graphic G1 may be adjacent the first longitudinal side edge 111a of the first belt 106. In some configurations, the first end edge 512 of the first graphic G1 may be positioned longitudinally outboard of the inner lateral end edge 107b of the first belt 106, and/or the second end edge 514 of the first graphic G1 may be positioned laterally inboard of the first longitudinal side edge 111a of the first belt 106. In some configurations, the first end edge 512 of the first graphic G1 may be coextensive with a portion of the inner lateral end edge 107b of the first belt 106, and/or the second end edge 514 of the first graphic G1 may be coextensive with a portion of the first longitudinal side edge 111a of the first belt 106. As mentioned above, the inner lateral edge 107b of the first elastic belt 106 may include non-linear or curved portions, and as such, the first end edge 512 of the first graphic G1 may also be non-linear or curved. Also, in some configurations, the second side edge 518 of the first graphic G1 may be designed to provide the appearance of a shaped inner lateral edge 107b.

As discussed above, the first graphic G1 is printed on the printed belt substrate 600 of the first belt 106. And it is to be appreciated that the first end edge 512 of the first graphic G1 may be located in various positions relative the inner lateral edge 600' of the printed belt substrate 600 and/or inner lateral edge 107b of the first belt 106. For example, as shown in FIG. 4A1, the first graphic G1 may be printed on the outer substrate layer 162, which is also shown as the printed belt substrate 600 in FIG. 4A1. And the first end edge 512 of the first graphic G1 may be positioned longitudinally outboard of an inner lateral end edge 600' of the printed belt substrate 600. In particular, the first end edge 512 is positioned longitudinally outboard of and separated from the inner lateral end edge 600' of the printed belt substrate 600 by a distance Dlong1a. In some embodiments, such as shown in FIG. 4A1, the inner lateral edge 600' of the printed substrate 600 may also be positioned longitudinally outboard of the inner lateral edge 107b of the first belt 106. In another example shown in FIG. 4A2, the first end edge 512 of the first graphic G1 may be coextensive and coincident with a portion of the inner lateral end edge 600' of the printed belt substrate 600. In yet another configuration shown in FIG. 4A3, the first end edge 512 of the first graphic G1 may be coextensive and coincident with a portion of the inner lateral end edge 600' of the printed belt substrate 600, and the inner lateral end edge 600' of the printed belt substrate 600 may also define the inner lateral edge 107b of the first belt 106.

With continued reference to FIGS. 2B, 4B 1, and 5B, the second graphic G2 defines a general stripe shape and extends from a first end edge 520 to a second end edge 522, and has a width Wg2 at the first end edge 520 defined by a distance extending laterally between a first side edge 524 and a second side edge 526 of the second graphic G2. In addition, the first side edge 524 of the second graphic G2 is laterally outboard relative the longitudinal axis 124 from the first side edge 604' of the printed chassis substrate 604 and laterally inboard relative the longitudinal axis 124 of the second side edge 526 of the second graphic G2. The first end edge 520 of the second graphic G2 extends between the first side edge 524 and the second side edge 526 adjacent the inner lateral end edge 602' of the printed belt substrate 602 of the second belt 108, and the second end edge 526 of the second graphic G2 may be adjacent the first longitudinal side edge 113a of the second belt 108. In some configurations, the first end edge 520 of the second graphic G2 may be positioned longitudinally outboard of the inner lateral end edge 109b of the second belt 108, and/or the second end edge 522 of the second graphic G2 may be positioned laterally inboard of the first longitudinal side edge 113a of the second belt 108. In some configurations, the first end edge 520 of the second graphic G2 may be coextensive with a portion of the inner lateral end edge 109b of the second belt 108, and/or the second end edge 522 of the second graphic G2 may be coextensive with a portion of the first longitudinal side edge 113a of the second belt 108. As mentioned above, the inner lateral edge 109b of the second elastic belt 108 may include non-linear or curved portions, and as such, the first end edge 520 of the second graphic G2 may also be non-linear or curved. Also, in some configurations, the second side edge 526 of the second graphic G2 may be designed to provide the appearance of a shaped inner lateral edge 109b.

As discussed above, the second graphic G2 is printed on the printed belt substrate 602 of the second belt 108. And it is to be appreciated that the first end edge 520 of the second graphic G2 may be located in various positions relative the inner lateral edge 602' of the printed belt substrate 602 and/or inner lateral edge 109b of the second belt 108. For example, as shown in FIG. 4B1, the second graphic G2 may be printed on the outer substrate layer 162, which is also shown as the printed belt substrate 602 in FIG. 4B1. And the first end edge 520 of the second graphic G2 may be positioned longitudinally outboard of an inner lateral end edge 602' of the printed belt substrate 602. In particular, the first end edge 520 is positioned longitudinally outboard of and separated from the inner lateral end edge 602' of the printed belt substrate 602 by a distance Dlong2a. In some embodiments, such as shown in FIG. 4B1, the inner lateral edge 602' of the printed substrate 602 may also be positioned longitudinally outboard of the inner lateral edge 109b of the second belt 108. In another example shown in FIG. 4B2, the first end edge 520 of the second graphic G2 may be coextensive and coincident with a portion of the inner lateral end edge 602' of the printed belt substrate 602. In yet another configuration shown in FIG. 4B3, the first end edge 520 of the second graphic G2 may be coextensive and coincident with a portion of the inner lateral end edge 602' of the printed belt substrate 602, and the inner lateral end edge 602' of the printed belt substrate 602 may also define the inner lateral edge 109b of the second belt 108.

It is to be appreciated that the widths Wg1, Wg2 of the first graphic G1 and the second graphic G2 may vary. For example, as shown in FIGS. 4A1-5B, the width Wg1 of the first graphic G1 may be less than the pitch length PL of the first belt 106, and the width Wg2 of the second graphic G2 may be less than the pitch length PL of the second belt 108. In some embodiments, the widths Wg1, Wg2 may be expressed in terms relative to the pitch lengths PL of the first and/or second belts 106, 108. For example, in some embodiments, the pitch lengths PL of the first and/or second belts 106, 108 may be from about 5 to about 500 times the widths Wg1 and/or Wg2. In addition, the widths Wg1, Wg2 of the first and second graphics G1, G2 may also be equal to each other. It is also to be appreciated that in some embodiments, the widths Wg1 and/or Wg2 may be the nominal width of a printed line.

Referring again to FIGS. 2B and 4A1-5B, the chassis graphic Gc defines a general stripe shape and extends longitudinally along the chassis 102 from a first end edge 528 to a second end edge 530. As shown in FIGS. 4A1-4A3, the first end edge 528 extends between a first side edge 532 and a second side edge 534. As such, the chassis graphic Gc defines a length Lgc1 at the first end edge 528 defined by a distance extending longitudinally between the first side edge 532 and the second side edge 534. In addition, the first side edge 532 of the chassis graphic Gc is longitudinally inboard relative the lateral axis 126 from the inner lateral edge 600' of the printed belt substrate 600 of the first belt 106 and longitudinally outboard relative the lateral axis 126 of the second side edge 534 of the chassis graphic Gc. As shown in FIGS. 4B1-4B3, the second end edge 530 extends between the first side edge 532 and the second side edge 534. As such, the chassis graphic Gc defines a length Lgc2 at the second end edge 530 defined by a distance extending longitudinally between the first side edge 532 and the second side edge 534. In addition, the second side edge 532 of the chassis graphic Gc is longitudinally inboard relative the lateral axis 126 from the inner lateral edge 602' of the printed belt substrate 602 of the second belt 108 and longitudinally outboard relative the lateral axis 126 of the second side edge 534 of the chassis graphic Gc.

In some configurations, the first end edge 528 and the second end edge 530 of the chassis graphic Gc may both extend between the first side edge 532 and the second side edge 534 adjacent the first longitudinal side edge 128 of the chassis 102. In some configurations, the first end edge 528 of the chassis graphic Gc may be positioned away from the first longitudinal side edge 128 of the chassis 102, and/or the second end edge 530 of the chassis graphic Gc may be positioned away from the first longitudinal side edge 128 of the chassis 102. For example, the first end edge 528 of the chassis graphic Gc may be positioned laterally inboard of and separated from the first longitudinal side edge 128 of the chassis 102, and/or the second end edge 530 of the chassis graphic Gc may be positioned laterally inboard of and separated from the first longitudinal side edge 128 of the chassis 102. It is also to be appreciated that in some embodiments, the first end edge 528 and/or the second end edge 530 of the chassis graphic Gc may be coextensive with a portion of the first longitudinal side edge 128 of the chassis 102.

As discussed above, the chassis graphic Gc is printed on the printed chassis substrate 604 of the chassis 102. And it is to be appreciated that the first end edge 528 of the chassis graphic Gc may be located in various positions relative the longitudinal edge 604' of the printed chassis substrate 604 and/or first longitudinal edge 128 of the chassis 102. As discussed above and as shown in FIGS. 4A1 and 4B1, the chassis 102 include various substrate layers, one of which may be configured as the printed chassis substrate 604. For example, the backsheet 136 may include an inner substrate 136a, such as a film layer substrate, and an outer substrate 136b, such as a nonwoven layer substrate. As such, the chassis graphic Gc is printed on the printed chassis substrate 604, which may also be the inner substrate 136a of the backsheet 136. And the first end edge 528 and/or the second end edge 530 of the chassis graphic Gc may be positioned laterally inboard of a longitudinal side edge 604' of the printed chassis substrate 604. In particular, the first end edge 528 may be positioned laterally inboard of and separated from the inner longitudinal side edge 604' of the printed chassis substrate 604 by a distance Dlat1a. And the second end edge 530 may be positioned laterally inboard of and separated from the inner longitudinal side edge 604' of the printed chassis substrate 604 by a distance Dlat2a. In some embodiments, such as shown in FIGS. 4A1 and 4B1, the longitudinal side edge 604' of the printed substrate 604 may also define the first longitudinal side edge 128 of the chassis 102. In other examples shown in FIGS. 4A2 and 4B2, the longitudinal side edge 604' of the printed substrate 604 may also be positioned laterally inboard the first longitudinal side edge 128 of the chassis 102. As such, it is also to be appreciated that various chassis components and/or substrates thereof that are devoid of printing may extend laterally outboard of the longitudinal side edge 604' of the printed substrate 604 to the chassis side edge 128, such as for example, portions of a topsheet 138, backsheet 136, and/or leg cuffs 156. In yet other configurations shown in FIGS. 4A3 and 4B3, the first end edge 528 and/or the second end edge 530 of the chassis graphic Gc may be coextensive and coincident with a portion of the longitudinal side edge 604' of the printed chassis substrate 604, and the longitudinal side edge 604' of the printed substrate 604 may also be positioned laterally inboard the first longitudinal side edge 128 of the chassis 102.

It is also to be appreciated that the chassis graphics Gc may be configured in various different designs and sizes. For example, the lengths Lgc1, Lgc2 of the chassis graphic Gc may vary. In some embodiments, the length Lgc1 of the chassis graphic Gc may be equal to or substantially equal to the length Lgc2. In some embodiments, the length Lgc1 of the chassis graphic Gc may be equal to or substantially equal to the width Wg1 of the first graphic G1. And in some embodiments, the length Lgc1 of the chassis graphic may be equal to or substantially equal to the width Wg2 of the second graphic G2. In some embodiments, the lengths Lgc1, Lgc2 and/or widths Wg1, Wg2 may be different. Also, as shown in FIGS. 5A and 5B, the chassis 102 may define a width CW extending between the first longitudinal edge 128 and the second longitudinal edge 130. It is to be appreciated that the chassis width CW may or may not vary longitudinally along the length of the chassis 102. As such, the chassis width CW may be the same or different along inner lateral edges 107b, 109b of the first and second belts 106, 108. Further, the chassis graphic Gc may be printed on various chassis components, such as the backsheet 136, and may be printed prior to or during assembly of the chassis components. And as discussed above, the chassis graphic Gc may be printed on a backsheet film layer that is subsequently covered by a nonwoven layer such that the chassis graphic Gc is visible through the nonwoven layer.

As discussed above and as shown in FIGS. 2B and 4A1-4A3, the first region 502 of the design 500 is separated from the third region 506 by the first discontinuous region 508, which is devoid of printing. As shown in detail in FIGS. 4A1-4A3, the first discontinuous region 508 may include a first side edge 536, a second side edge 538, a third side edge 540, and a fourth side edge 542. The first side edge 536 may be coextensive and conterminous with the first end edge 512 of the first graphic G1, and the second side edge 538 may be coextensive and coterminous with the first end edge 528 of the chassis graphic Gc. The third side edge 540 may extend from the intersection of the first end edge 512 and the first side edge 516 of the first graphic G1 to the intersection of the first end edge 528 and the first side edge 532 of the chassis graphic Gc. And the fourth side edge 542 may extend from the intersection of the first end edge 512 and the second side edge 518 of the first graphic G1 to the intersection of the first end edge 528 and the second side edge 534 of the chassis graphic Gc. As such, the first side edge 536, the second side edge 538, the third side edge 540, and the fourth side edge 542 of the first discontinuous region 508 of the design 500 may be connected together so as to define a substantially trapezoidal-shaped perimeter P1 devoid of printing. In turn, the substantially trapezoidal-shaped perimeter P1 may extend between the first end edge 512 of the first graphic G1 and the first end edge 528 of the chassis graphic Gc, defining an imaginary continuous extension of an established direction of the first graphic G1 to the chassis graphic Gc.

As discussed above and as shown in FIGS. 2B and 4B1-4B3, the second region 504 of the design 500 is separated from the third region 506 by the second discontinuous region 510, which is devoid of printing. As shown in detail in FIGS. 4B1-4B3, the second discontinuous region 510 may include a first side edge 544, a second side edge 546, a third side edge 548, and a fourth side edge 550. The first side edge 544 may be coextensive and conterminous with the first end edge 520 of the second graphic G2, and the second side edge 546 may be coextensive and coterminous with the second end edge 530 of the chassis graphic Gc. The third side edge 548 may extend from the intersection of the first end edge 520 and the first side edge 524 of the second graphic G2 to the intersection of the second end edge 530 and the first side edge 532 of the chassis graphic Gc. And the fourth side edge 550 may extend from the intersection of the first end edge 520 and the second side edge 526 of the second graphic G2 to the intersection of the second end edge 530 and the second side edge 534 of the chassis graphic Gc. As such, the first side edge 544, the second side edge 546, the third side edge 548, and the fourth side edge 550 of the first discontinuous region 510 of the design 500 may be connected together so as to define a substantially trapezoidal-shaped perimeter P2 devoid of printing. In turn, the substantially trapezoidal-shaped perimeter P2 may extend between the first end edge 520 of the second graphic G2 and the second end edge 530 of the chassis graphic Gc, defining an imaginary continuous extension of an established direction of the second graphic G2 to the chassis graphic Gc.

As previously mentioned, including first and/or second discontinuous regions 508, 510 as part of the design 500 help to provide the appearance that the first graphic G1, second graphic G2, and chassis graphic Gc on the assembled first belt 106, second belt 108, and chassis 102 form a contiguous design. In addition, the first and/or second discontinuous regions 508, 510 of the design 500 help to mitigate the need during the manufacturing process to precisely align the graphics G1, G2, and Gc on first belt 106, second belt 108, and chassis 102 to form a contiguous design.

As shown in FIGS. 4A1-4A3, the intersection of the first end edge 512 and the first side edge 516 of the first graphic G1 may be positioned laterally outboard with respect to the longitudinal axis 124 of the longitudinal side edge 604' of the printed chassis substrate 604 of the chassis 102 by a distance Dlat1. And the intersection of the first end edge 528 and the first side edge 532 of the chassis graphic Gc may be positioned longitudinally inboard with respect to the lateral axis 126 of the inner lateral end edge 600' of the printed belt substrate 600 of the first belt 106 by a distance Dlong1. Similarly, as shown in FIGS. 4B1-4B3, the intersection of the first end edge 520 and the first side edge 524 of the second graphic G2 may be positioned laterally outboard with respect to the longitudinal axis 124 of the first longitudinal side edge 604' of the printed chassis substrate 604 of the chassis 102 by a distance Dlat2. And the intersection of the first end edge 528 and the first side edge 532 of the chassis graphic Gc may be positioned longitudinally inboard with respect to the lateral axis 126 inner lateral end edge 602' of the printed belt substrate 602 of the second belt 108 by a distance Dlong2. Thus, as discussed below with reference to FIG. 6, the distances Dlong1 and Dlong2 may allow for some inconsistent and/or imprecise cross directional CD placement of the chassis 102 relative to the first and/or second belts 106, 108 during manufacture. Similarly, the distances Dlat1 and Dlat2 may allow for some inconsistent and/or imprecise machine directional MID placement of the chassis 102 relative to the first and/or second belts 106, 108 during manufacture. It is to be appreciated that the distances Dlat1, Dlong1, Dlat2, Dlong2 may vary depending on various factors, such as the precision and/or consistency of the manufacturing processes used to assemble the belts 106, 108 and chassis 102. In some embodiments, the distances Dlat1, Dlong1, Dlat2, and/or Dlong2 may be equal to or greater than zero and less than about 30 mm. Thus, in contrast to the example discussed above with reference to FIGS. 2B1 and 2B2, the design 500 with the first and/or second discontinuous regions 508, 510 and the distances Dlat1, Dlong1, Dlat2, and/or Dlong2 such as shown in FIGS. 2B, 4A1-4A3, and 4B1-4B3 help provide the ability to combine separate components in such a manner so as to functionally reduce noticeable visible results of imprecise and/or inconsistent manufacturing operations performed in areas where the graphics are located.

Although the above discussion is mainly provided in the context of the first graphic G1, the second graphic G2, and the chassis graphic Gc such as shown in FIG. 2B, it is to be appreciated that the diaper pant 100 may include various other graphics G. For example, as shown in FIG. 2B, the diaper pant 100 may include additional graphics G1, G2, and Gc that are mirrored to the first graphic G1, the second graphic G2, and the chassis graphic Gc relative the longitudinal axis 124. In addition, the graphics may be positioned relative to each other on the various diaper components to provide designs with discontinuous regions and distances Dlat1 and Dlat2 that correspond with each other relative the longitudinal axis 124. For example, as shown in FIG. 5A, the graphics G1 on the first belt 106 may be separated from each other in a lateral direction by a distance that is greater than the chassis width CW. Similarly, as shown in FIG. 5B, the graphics G2 on the second belt 108 may be separated from each other in a lateral direction by a distance that is greater than the chassis width CW. It is also to be appreciated that the graphics may be also visible when viewed from outer surfaces and/or inner surfaces of various substrates and components.

Figure 5C:
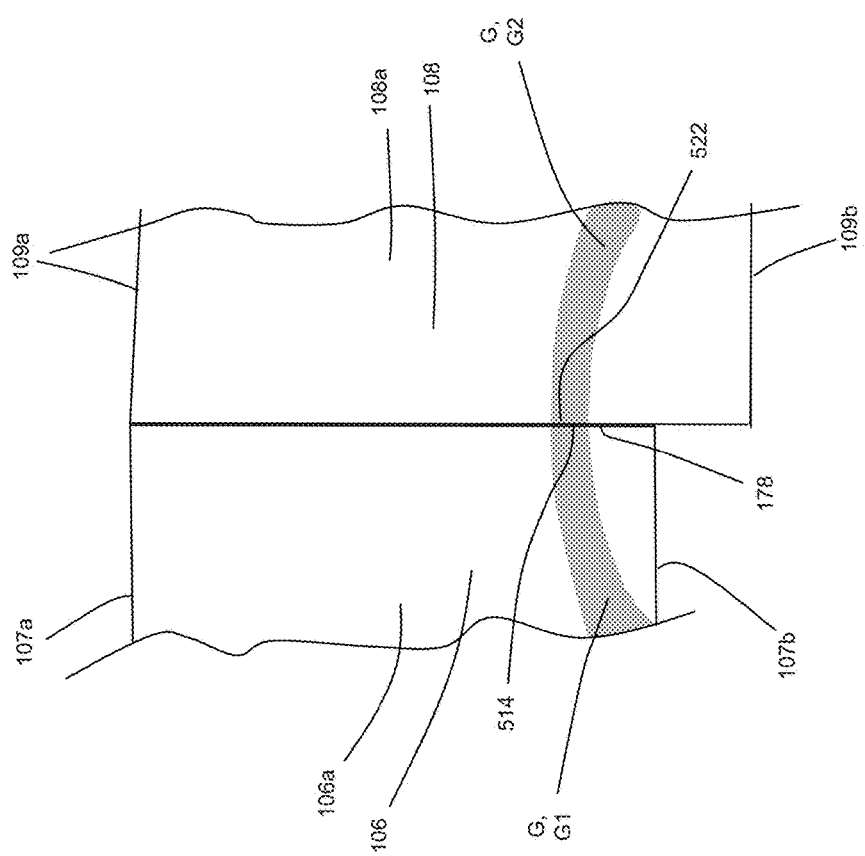
FIG. 5C is a detailed side view of aligned belt graphics of the absorbent article from FIG. 5A.

It is to be appreciated that although portions of graphic designs may include discontinuous regions, other portions of the graphics on various components of the diaper 100 may be assembled such that the graphics G are aligned with each other to create the appearance of a contiguous design that extends across the assembled components. For example, FIG. 5C shows a plan view of the first side seam 178 of the assembled diaper pant 100 from FIGS. 2B, 5A, and 5B. As shown in FIG. 5C, the first end region 106a of the first belt 106 is connected with the first end region 108a of the second belt 108 such that the second end edge 514 of the first graphic G1 is aligned with the second end edge 530 of the second graphic G2 to form a contiguous design extending across the side seam 178.

As discussed above with reference to FIGS. 2A-3B, the first belt 106 and/or the second belt 108 may include elastic material, such as elastic strands 168. In addition, the chassis 102 may include elastic material such as elasticized leg cuffs 156. During the assembly process, the elastic material in the first and/or second belts 106, 108 and/or the chassis 102 may be positioned in an absorbent article 100 under tension and may be held under tension. However, such tension on the elastic material may be removed before or during the assembly process, allowing the elastic material in the first and/or second belts 106, 108 and/or the chassis 102 to contract. As such, contraction of the elastic material may deform the first and/or second belts 106, 108 and/or the chassis 102 so as to cause the first region 502, second region 504, and/or third region 506 of the design 500 to intersect or mate so as to form a contiguous design across the chassis 102 and the first belt 106 and/or across the chassis 102 and the second belt 108. For example, FIG. 4A4 shows a detailed view of the intersection of the chassis 102 and first belt 106 once tension is removed from elastic material in the first belt and/or chassis and has contracted. As shown in FIG. 4A4, contraction of the elastic material may deform the chassis 102 and the first elastic belt 106, causing the first graphic G1 and the chassis graphic Gc to mate and form a contiguous design extending across the chassis 102 and the first belt 106. It is to be appreciated that the first graphic G1 and the chassis graphic Gc may be mated in such a manner that the first discontinuous region 508, such as shown in FIGS. 4A1-4A3, is partially or completely eliminated. In some configurations, the perimeter P1 of the first discontinuous region 508 may be deformed from a substantially trapezoidal shape to a substantially triangular shape. In some configurations, the first graphic G1 and the chassis graphic Gc may overlap one another. In addition, the first side edge 516 of the first graphic G1 and the first side edge 532 of the chassis graphic Gc may be aligned or offset from each other, and the second side edge 518 of the first graphic G1 and the first side edge 534 of the chassis graphic Gc may be aligned or offset from each other. Further contraction of the elastics can reduce the values of the dimensions of Dlat1 and/or Dlong1, referred to in FIGS. 4A1-4A3, to zero.

As shown in FIG. 4B4, contraction of the elastic material may deform the chassis 102 and the second elastic belt 108, causing the second graphic G2 and the chassis graphic Gc to mate and form a contiguous design extending across the chassis 102 and the second belt 108. It is to be appreciated that the second graphic G2 and the chassis graphic Gc may be mated in such a manner that the second discontinuous region 510, such as shown in FIGS. 4B1-4B3, is partially or completely eliminated. In some configurations, the perimeter P2 of the second discontinuous region 510 may be deformed from a substantially trapezoidal shape to a substantially triangular shape. In some configurations, the second graphic G2 and the chassis graphic Gc may overlap one another. In addition, the first side edge 524 of the second graphic G2 and the first side edge 532 of the chassis graphic Gc may be aligned or offset from each other, and the second side edge 526 of the second graphic G2 and the first side edge 534 of the chassis graphic Gc may be aligned or offset from each other. Further contraction of the elastics can reduce the values of the dimensions of Dlat2 and/or Dlong2, referred to in FIGS. 4B1-4B3, to zero.

Figure 6:
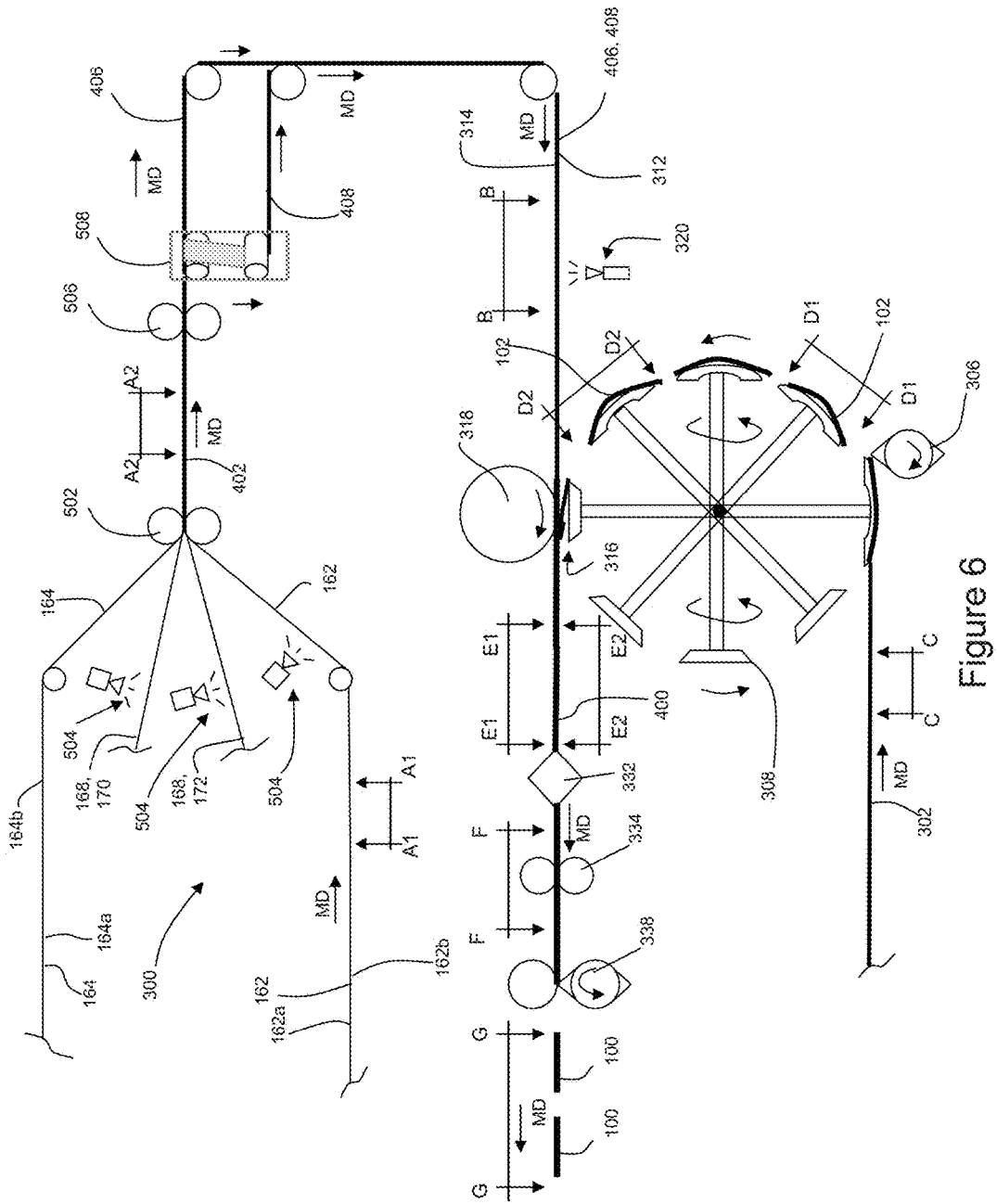
FIG. 6 is a schematic side view of a converting apparatus adapted to manufacture pre-fastened, pant diapers.

As previously mentioned, substrates and/or components that may be incorporated into manufactured absorbent articles, such as shown in FIG. 2B, include graphics that may be positioned and/or printed in such a manner so as to reduce noticeable visible results of imprecise and/or inconsistent manufacturing operations performed in areas where the printing is located. It is to be appreciated that various apparatuses and methods according to the present disclosure may be utilized to assemble various components of prefastened pant diapers 100 described herein. For example, FIG. 6 shows a schematic view of a converting apparatus 300 adapted to manufacture pant diapers 100. The method of operation of the converting apparatus 300 may be described with reference to the various components of pant diapers 100 described above and shown in FIGS. 1A, 1B, 2A, and 2B. Although the following methods are provided in the context of the diaper 100 shown in FIGS. 1A, 1B, 2A, and 2B, it is to be appreciated that various embodiments of diaper pants can be manufactured according to the methods disclosed herein, such as for example, the absorbent articles disclosed in U.S. Pat. No. 7,569,039; U.S. Patent Publication Nos. 2005/0107764 A1, 2012/0061016 A1, and 2012/0061015 A1, which are all hereby incorporated by reference herein.

As described in more detail below, the converting apparatus 300 shown in FIG. 6 operates to advance first and second elastic belt laminates 406, 408 along a machine direction MD. In addition, a continuous length of chassis assemblies 302 are advanced in a machine direction MD and cut into discrete chassis 102 such that the longitudinal axis 124 of each chassis 102 is parallel with the machine direction MD. The discrete chassis 102 are then turned to advance the discrete chassis 102 along the machine direction MD such that the lateral axis 126 of each chassis 102 is parallel with the machine direction MD. The discrete chassis 102 are also spaced apart from each other along the machine direction MD. Opposing waist regions 116, 118 of the spaced apart chassis 102 are then connected with continuous lengths of advancing first and second elastic belt laminates 406, 408. The chassis 102 may then be folded along the lateral axis, or parallel to the lateral axis, to bring the first and second elastic belt laminates 406, 408 into a facing relationship, and the first and second elastic belt laminates are bonded together with laterally opposing bonds 336. As discussed in more detail below, the first and second elastic belt laminates may be bonded together with adjacent bonds 336a, 336b intermittently spaced along the machine direction MD. It is to be appreciated that the bonds 336a, 336b may be configured as permanent and/or refastenable bonds. And each bond 336a, 336b may be a discrete bond site extending contiguously in a cross direction CD across a width of the first and second elastic belt laminates and/or may include a plurality of relatively small, discrete bond sites arranged in the cross direction. The first and second continuous elastic laminates 406, 408 are then cut in the cross direction CD between adjacent bonds 336a, 336b to create discrete pant diapers 100, such as shown in FIGS. 1A and 1B. During the assembly process, the chassis 102 and the elastic laminates 406, 408 may be assembled such that the respective graphics are aligned to provide designs 500 such as described above that extend across more than one of the assembled elastic belts 106, 108 and/or chassis 102.

As shown in FIG. 6, a first continuous substrate layer in the form of a continuous length of outer layer belt substrate 162; a second continuous substrate layer in the form of a continuous length of inner layer belt substrate 164; and elastics 168 are combined to form a continuous elastic laminate 402 in the form of a belt material. More particularly, continuous lengths of outer layer belt substrate 162, inner layer belt substrate 164, outer elastic strands 170 and inner elastic strands 172 are advanced in a machine direction MD and combined at nip rolls 502 to form the continuous elastic laminate 402. Before entering the nip rolls 502, the outer layer belt substrate 162 and/or the inner layer belt substrate 164 may be printed with graphics G. It is to be appreciated that the graphic printing may be done during the assembly process and/or may done separate to the assembly process, such as for example, printing the substrates off line wherein the printed substrates may be stored until needed for production.

As shown in FIGS. 6, 7A1, and 7A2, the outer belt substrate 162 includes first surface 162a and an opposing second surface 162b, and defines a width W in the cross direction CD between opposing first and second longitudinal edges 163a, 163b. And the inner belt substrate 164 includes first surface 164a and an opposing second surface 164b, and defines a width in the cross direction CD between opposing first and second longitudinal edges 165a, 165b. As shown in FIG. 7A2, the width W of the outer belt substrate 162 may be greater than the width of the inner belt substrate 164. And the width W of the outer belt substrate 162 may also define the width W of the elastic laminate 402. It is to be appreciated that in some embodiments, the width of the inner belt substrate 164 may be the same as or greater than the width of the outer belt substrate 162.

With continued reference to FIG. 6, before entering the nip rolls 502, the outer elastic strands 170 and inner elastic strands 172 are stretched in the machine direction MD. In addition, adhesive 504 may be applied to the elastic strands 170, 172 as well as either or both of the continuous lengths of outer layer belt substrate 162 and inner layer belt substrate 164 before entering nip rolls 502. As such, the elastic strands 168 are bonded between the first surface 162a of the outer layer belt substrate 162 and the first surface 164a of inner layer belt substrate 164 at the nip rolls 502. Further, adhesive 504 may be applied intermittently along the lengths of the inner elastic strands 172 and/or intermittently along the length of either or both of the continuous lengths of outer layer belt substrate 162 and inner layer belt substrate 164 before entering nip rolls 502. As such, the inner elastic strands 172 may be intermittently bonded to either or both of the continuous lengths of outer layer belt substrate 162 and inner layer belt substrate 164 along the machine direction MD. Thus, the continuous elastic laminate 402 may include non-bonded regions intermittently spaced between bonded regions along the machine direction MD, wherein the inner elastic strands 172 are not bonded to either the outer layer belt substrate 162 or inner layer belt substrate 164 in the non-bonded regions. And the inner elastic strands 172 are bonded to the outer layer belt substrate 162 and/or inner layer belt substrate 164 in the bonded regions. As such, the elastic strands 172 may be severed in the non-bonded regions in a subsequent process step. Although FIG. 6 shows an embodiment wherein the continuous elastic laminate 402 is formed by combining continuous lengths of outer layer belt substrate 162 and inner layer belt substrate 164 with elastic strands 168, it is to be appreciated the continuous elastic laminate 402 can be formed in various ways, such as disclosed in U.S. Pat. No. 8,440,043 and U.S. Patent Publication Nos. 2013/0255861 A1; 2013/0255862 A1; 2013/0255863 A1; 2013/0255864 A1; and 2013/0255865 A1.

As shown in FIGS. 6 and 7A1, the outer belt substrate 162 advances in the machine direction and may include graphics G printed on the first surface 162a of the outer layer belt substrate 162. As shown in FIG. 7A1, although the graphics G are printed on the first surface 162a of the outer layer belt substrate 162, the graphics G may be visible through the second surface 162b. It is also to be appreciated that the graphics G may be printed on either or both the first and second surfaces 162a, 162b of the outer belt substrate 162. It is also to be appreciated that graphics may be printed on either or both the first and second surfaces 164a, 164b of the inner belt substrate 164.

As shown in FIG. 7A1, the graphics G extend in the machine direction MD and the cross direction CD, wherein each graphic G defines a closed perimeter. In some embodiments, the width W of the belt substrate 162 and/or elastic laminate 402 may be from about 240 mm to about 600 mm. It is to also to be appreciated that the graphics G may be printed to have differing designs from each other along the machine direction MD and/or cross direction CD. Also shown in FIG. 7A1, the outer belt substrate 162, and thus the elastic laminate 402, may include first and second outer longitudinal regions 166a, 166b separated in the cross direction CD by a central region 166c. And the graphic G may be positioned entirely within the central region 166c of the elastic laminate 402. It is to be appreciated the widths of the regions 166a, 166b, 166c may vary. For example, in some embodiments, the central region 166c may be about 33% of the width W of the elastic laminate 402. In some embodiments, the first and second outer longitudinal regions 166a, 166b and/or the central region may each be about ⅓ of the width W of the elastic laminate 402.

Figure 7B:
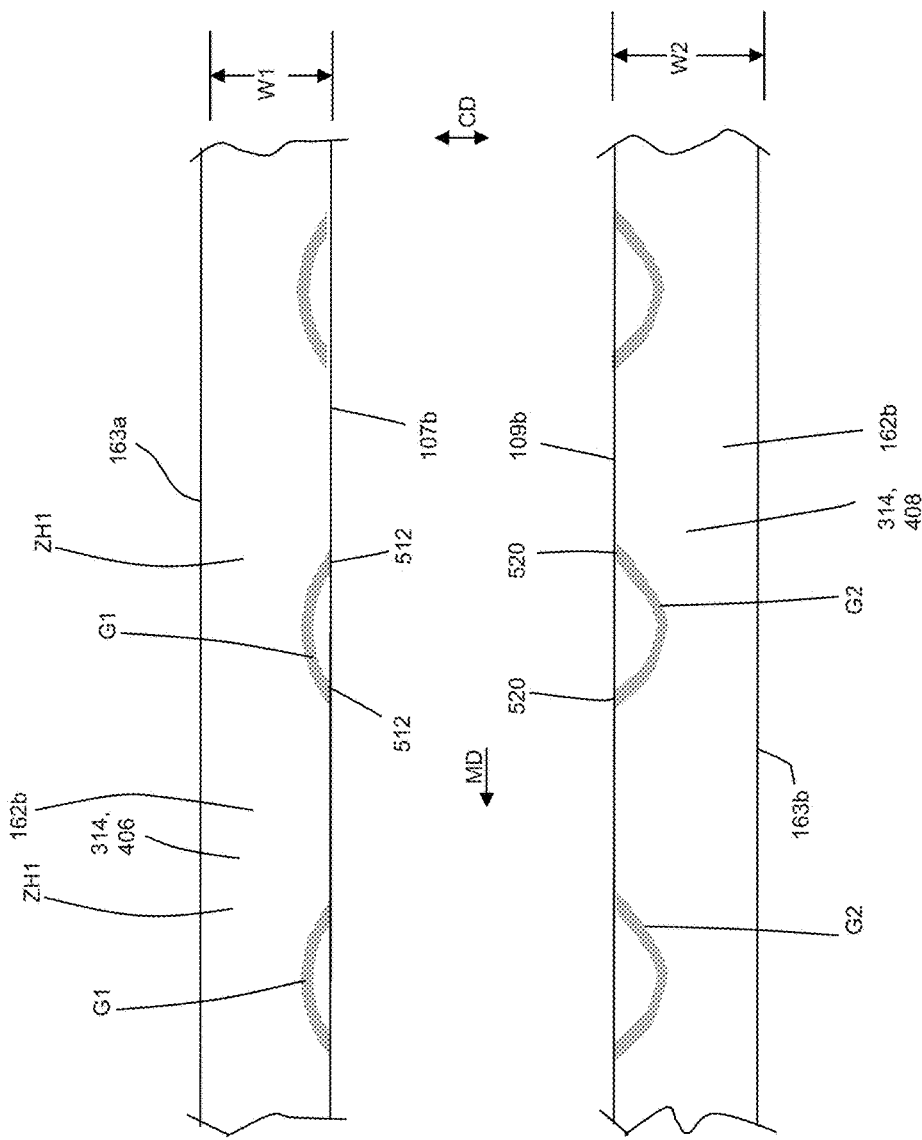
FIG. 7B is a view of continuous lengths of advancing first and second elastic belt laminates from FIG. 6 taken along line B-B.

With continued reference to FIGS. 6, 7A2, and 7B, from the nip rolls 502 the continuous elastic laminate 402 advances in the machine direction MD to a cutter 506 that cuts the continuous elastic laminate 402 into two continuous elastic belt laminates, referred to as a first elastic belt laminate 406 and a second elastic belt laminate 408. In particular, the cutter 506 operates to cut the elastic laminate 402 along the machine direction and through the graphic G to form the first continuous elastic laminate 406 and the second continuous elastic laminate 408. As such, the cutter 506 also operates to divide the graphic G into a first graphic G1 and a second graphic G2, wherein the first graphic is positioned on the first elastic laminate 406 and the second graphic G2 is positioned on the second elastic laminate 408. As such, a cut line created by the cutter 506 through the graphic G may create the first end edges 512, 520 of the first and second graphics G1, G2 discussed above. Also, as shown in FIG. 7B, the first elastic laminate 406 includes an inner longitudinal edge 107b and an outer longitudinal edge 107a, and the second elastic laminate 406 includes an inner longitudinal edge 109b and an outer longitudinal edge 109a. As shown in FIG. 7B, the first belt laminate 406 extends between the outer longitudinal edge 107a and the inner longitudinal edge 107b to define a width W1 in the cross direction CD. And the second belt laminate 408 extends between the outer longitudinal edge 109a and the inner longitudinal edge 109b to define a width W2 in the cross direction CD. It is to be appreciated that W2 may be greater than W1. It is also to be appreciated that in some configurations, W1 may be equal to or greater than W2. In some embodiments, the widths W1 and/or W2 may be from about 120 mm to about 300 mm.

It is also to be appreciated that the cutter 506 may be configured in various ways. For example, in some embodiments the cutter 506 may be a slitter or a die cutter that separates the belt material into two continuous belt substrates with either a straight line cut and/or a curved line cut. The cutter 506 may also be configured as a perforator that perforates the belt material with a line of weakness and wherein the belt material is separated along the line of weakness in a later step. From the cutter 506, the first and second belt laminates 406, 408 advance through a diverter 508 that separates the first and second belt substrates from each other in the cross direction CD, such as shown in FIG. 7B. The elastic strands 170, 172, and thus, the continuous length of first and second belt laminates 406, 408 are maintained in a stretched condition while advancing along the machine direction MD.

In some embodiments, the cut line through the elastic laminate 402 created by the cutter 506 may define the inner edge 107b of the first belt laminate 406 and/or the inner edge 109b of the second belt laminate 408. In some embodiments, the first belt laminate 406 and/or the second belt laminate 408 may advance from the cutter 506 to a folding apparatus adapted that folds the cut edges of the first and/or second belt laminates created by the cutter 506. As such, the inner edge 107b of the first belt laminate 406 and/or the inner edge 109b of the second belt laminate 408 may be defined by a fold line extending along the machine direction MD.

It is to be appreciated that the diverter 508 may be configured in various ways. For example, in some embodiments, the diverter 508 may include turn bars angled at 45 degrees or some other angle with respect to the machine direction. In some embodiments, the diverter may include cambered rollers. It is to be appreciated that the front and back belts may be formed by separate continuous lengths of belt material similar to the description above and as such would not require the slitting step or the diverting step. And in some embodiments, the front and back belts may be formed by slitting the outer belt substrate 162 and the inner belt substrate 164 along the machine direction MD before being combined with the elastic material 168.

In some embodiments, the diverter 508 may include a pivot or tracking table, such as for example, the FIFE-500 Web Guiding System, by Maxcess-FIFE Corporation, which can adjust the positions of the continuous length of first and second belt laminates 406, 408 in the cross direction CD. Other suitable pivot or tracking tables are available from Erhardt & Leimer, Inc. The diverter may also include instrumentation and web edge control features that allow for precise active control of the substrate positions.

As previously mentioned, the first belt laminate 406 is separated in the cross direction CD from the second belt laminate 408 to define a gap between the inner longitudinal edge 107b of the first belt laminate 406 and the inner longitudinal edge 109b of the second belt laminate 408. As discussed in more detail below, the first and second belt laminate 406, 408 advance from the diverter 508 to a nip 316 between the carrier apparatus 308 and a roll 318 to be combined with discrete chassis 102.

Referring now to FIGS. 6 and 7C, a continuous length of chassis assemblies 302 are advanced in a machine direction MD and define a width in a cross direction CD. The continuous length of chassis assemblies 302 may include absorbent assemblies 140 sandwiched between topsheet material 138 and backsheet material 136, leg elastics, barrier leg cuffs and the like. As shown in FIG. 7C, portion of the chassis assembly is cut-away to show a portion of the topsheet material 138 and an absorbent assembly 140. The continuous length of chassis assemblies 302 advance to a carrier apparatus 308 and are cut into discrete chassis 102 with knife roll 306, while advancing in the orientation shown in FIG. 7D1, wherein the longitudinal axis 124 of each chassis 102 is generally parallel with the machine direction MD.

As previously mentioned, the chassis 102 may also include graphics. For example, as shown in FIGS. 6 and 7C, the continuous length of chassis assemblies 302 are advanced in a machine direction MD may include chassis graphics Gc printed thereon. It is to be appreciated that the chassis graphics Gc may be printed on various chassis components, such as the backsheet 136, and may be printed prior to or during assembly of the chassis components. In some configurations, the chassis graphics Gc may be printed on a backsheet film layer that is subsequently covered by a nonwoven layer such that the chassis graphics are visible through the nonwoven layer. It is also to be appreciated that the various printing processes may be used to print the chassis graphics Gc, such as for example, ink jet, flexography, and/or gravure printing processes as discussed above.

It is also to be appreciated that the chassis graphics GC may be configured in various different designs. For example, as shown in FIG. 7C, the chassis graphics GC may be configured as laterally opposing first and second stripes Gc having discrete lengths separated from each other along the machine direction MD of the continuous length of chassis assemblies 302. As discussed above, the continuous length of chassis assemblies 302 may include absorbent assemblies 140 sandwiched between topsheet material 138 and backsheet material 136, leg elastics, barrier leg cuffs and the like. It is also to be appreciated that chassis graphics Gc may extend continuously across the chassis 102 and/or may be configured to intersect other graphics.

With continued reference to FIGS. 6 and 7D1, the continuous length of chassis assemblies 302 advance to the carrier apparatus 308 and are cut into discrete chassis 102 with knife roll 306, while advancing in the orientation shown in FIG. 7D1, wherein the longitudinal axis 124 of each chassis 102 is generally parallel with the machine direction MD. More particularly, the knife roll 306 operates to cut the continuous length of chassis assemblies 302 in the cross direction CD between graphics Gc. In some graphic embodiments wherein the chassis graphics Gc extend contiguously along the machine direction, the knife roll 306 operates to cut the continuous length of chassis assemblies 302 in the cross direction CD through the chassis graphics Gc. As shown in FIG. 7D1, the discrete chassis 102 may have a pitch length PLC extending between the first lateral end edge 144 and the second lateral end edge 146. In addition, the first end edges 528 of the chassis graphics Gc extend along the first and second longitudinal side edges 128, 130 of the chassis 102 adjacent the first lateral end edge 144, and the second end edges 530 of the chassis graphics Gc extend along the first and second longitudinal side edges 128, 130 of the chassis 102 adjacent the second lateral end edge 146. As previously discussed, the chassis graphic Gc defines a length Lgc1 at the first end edge 528 and defines a length Lgc2 at the second end edge 530. It is to be appreciated that lengths Lgc1, Lgc2 of the chassis graphics Gc may vary. In some embodiments, the lengths Lgc1, Lgc2 may be from about 4 mm to about 30 mm. In some embodiments, the lengths Lgc1, Lgc2 may also be expressed in terms relative to the pitch length PLC of the chassis 102. For example, in some embodiments, the pitch length PLC of the chassis 102 may be about 10 to about 500 times the lengths Lgc1, Lgc2. It is also to be appreciated that in some embodiments, the lengths Lgc1 and/or Lgc2 may be the nominal width of a printed line.

After the discrete absorbent chassis 102 are cut by the knife roll 306, the carrier apparatus 308 rotates and advances the discrete chassis 102 in the machine direction MD in the orientation shown in FIG. 7D1. While the chassis 102 shown in FIG. 7D1 is shown with the second laterally extending end edge 146 as a leading edge and the first laterally extending end edge 144 as the trailing edge, it is to be appreciated that in other embodiments, the chassis 102 may be advanced in other orientations. For example, the chassis may be oriented such that the second laterally extending end edge 146 is a trailing edge and the first laterally extending end edge 144 is a leading edge. The carrier apparatus 308 also rotates while at the same time changing the orientation of the advancing chassis 102. In changing the chassis orientation, the carrier apparatus 308 may turn each chassis 102 such that the lateral axis 126 of the chassis 102 is parallel or generally parallel with the machine direction MD, such as shown in FIG. 7D2. The carrier apparatus 308 may also change the speed at which the chassis 102 advances in the machine direction MD to a different speed. FIG. 7D2 shows the orientation of the chassis 102 on the carrier apparatus 308 while advancing in the machine direction MD. More particularly, FIG. 7D2 shows the chassis 102 with the lateral axis 126 of the chassis 102 generally parallel with the machine direction MD, and wherein the second longitudinal side edge 130 is the leading edge and the first longitudinal side edge 128 is the trailing edge. It is to be appreciated that various forms of carrier apparatuses may be used with the methods herein, such as for example, the carrier apparatuses disclosed in U.S. Pat. No. 7,587,966 and U.S. Patent Publication Nos. 2013/0270065 A1; 2013/0270069 A1; 2013/0270066 A1; and 2013/0270067 A1. In some embodiments, the carrier apparatus 308 may rotate at a variable angular velocity that may be changed or adjusted by a controller in order to change the relative placement of the chassis 102 and the advancing belt laminates 406, 408.

As discussed below with reference to FIGS. 6, 7E1, 7E2, 7F, 7G1, and 7G2, the chassis 102 are transferred from the carrier apparatus 308 and combined with advancing, continuous lengths of belt laminates 406, 408, which are subsequently cut to form first and second elastic belts 106, 108 on diapers 100.

As shown in FIGS. 6, 7B, 7E1, and 7E2, the chassis 102 are transferred from the carrier apparatus 308 to a nip 316 between the carrier apparatus 308 and a roll 318 where the chassis 102 is combined with continuous lengths of advancing front belt 406 and back belt 408. The front belt laminate 406 and the back belt laminate material 408 each include a wearer facing surface 312 and an opposing garment facing surface 314. As such, the second surface 162b of the outer layer belt substrate 162 may define some or all the garment facing surface 314, and the second surface 164b of the inner layer belt substrate 164 may define some or all the wearer facing surface 312. The wearer facing surface 312 of the first belt laminate 406 may be combined with the garment facing surface 134 of the chassis 102 along the first waist region 116, and the wearer facing surface 312 of the second belt laminate 408 may be combined with the garment facing surface 134 of the chassis 102 along the second waist region 118. As shown in FIG. 6, adhesive 320 may be intermittently applied to the wearer facing surface 312 of the first and second belt laminates 406, 408 before combining with the discrete chassis 102 at the nip 316 between roll 318 and the carrier apparatus 308.

As shown in FIGS. 6, 7B, and 7E1, the chassis 102 are transferred from the carrier apparatus 308 to the nip 316 between the carrier apparatus 308 and the roll 318 where the chassis 102 is combined with continuous lengths of advancing front belt 406 and back belt 408. As shown in FIG. 7E1, each chassis 102 may be combined with the front belt 406 and back belt 408 such that the chassis 102 and associated graphics Gc are positioned between the belt graphics G1, G2 to form discontinuous regions 508, 510 as discussed above with reference to FIGS. 4A1-4A3 and 4B1-4B3. As such, designs are formed with the discontinuous regions 508, 510 extending between the chassis graphics Gc and the belt graphics G1, G2 that are positioned in areas where the front belt 406, back belt 408, and chassis 102 are combined. Thus, designs with such discontinuous regions may help reduce the noticeable results of imprecise placement of the chassis 102 onto the front and/or back belts 406, 408, thereby helping to mitigate the noticeable appearance of disjointed and/or misaligned graphics on the chassis 102, front belt 406, and/or back belt 408.

Referring back to FIGS. 6, 7E1, and 7E2 a continuous length of absorbent articles 400 are defined by multiple discrete chassis 102 spaced from each other along the machine direction MD and connected with each other by the second belt laminate 408 and the first belt laminate 406. As shown in FIG. 6, the continuous length of absorbent articles 400 advances from the edge transformation apparatus 331 to a folding apparatus 332. At the folding apparatus 332, each chassis 102 is folded in the cross direction CD parallel to or along a lateral axis 126 to place the first waist region 116, and specifically, the inner, body facing surface 132 into a facing, surface to surface orientation with the inner, body surface 132 of the second waist region 118. The folding of the chassis also positions the wearer facing surface 312 of the second belt laminate 408 extending between each chassis 102 in a facing relationship with the wearer facing surface 312 of the first belt laminate 406 extending between each chassis 102.

Figure 7F:
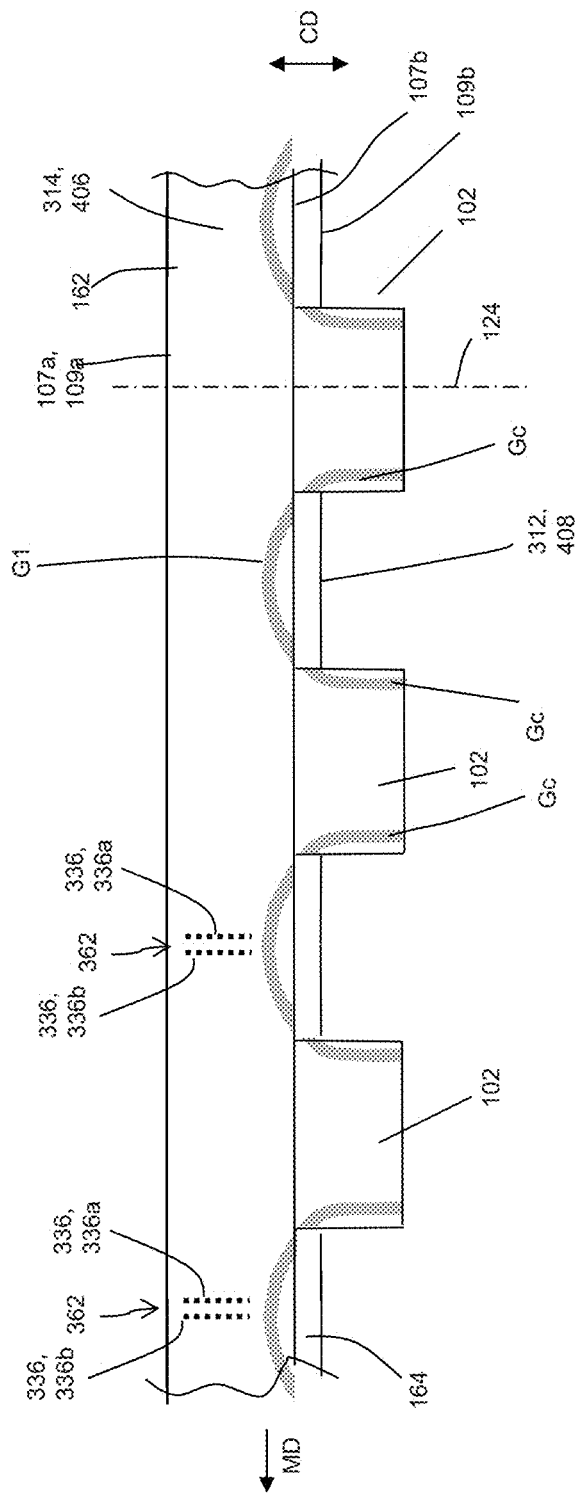
FIG. 7F is a view of folded multiple discrete chassis with the first and second elastic belt laminates in a facing relationship from FIG. 6 taken along line F-F.

As shown in FIGS. 6 and 7F, the folded discrete chassis 102 connected with the first and second belt laminates 406, 408 are advanced from the folding apparatus 332 to a bonder apparatus 334. The bonder apparatus 334 operates to bond an overlap area 362, thus creating discrete bonds 336a, 336b. The overlap area 362 includes a portion of the second belt laminate 408 extending between each chassis 102 and a portion of the first belt laminate 406 extending between each chassis 102. It is to be appreciated that the bonder apparatus 334 may be configured in various ways to create bonds 336a, 336b in various ways, such as for example with heat, adhesives, pressure, and/or ultrasonics. It is also to be appreciated that in some embodiments, the apparatus 300 may also be configured to refastenably bond the overlap area 362, in addition to or as opposed to permanently bonding the overlap area 362. Thus, the discrete bonds 336a, 336b may be configured to be refastenable, such as with hooks and loops.

Referring now to FIGS. 6, 7G1, and 7G2, the continuous length of absorbent articles 400 are advanced from the bonder 334 to a cutting apparatus 338 where the first belt laminate 406 and the second belt laminate 408 are cut along the cross direction CD between adjacent bonds 336a, 336b to create discrete absorbent articles 100. As shown in FIGS. 7G1 and 7G2, the first belt laminate 406 and the second belt laminate 408 are cut into discrete pieces to form the front and back elastic belts 106, 108, each having a pitch length, PL, extending along the machine direction MD. As such, bond 336a may correspond with and form a first side seam 178 on an absorbent article 100, and the bond 336b may correspond with and form a second side seam 180 on a subsequently advancing absorbent article. In addition, the graphics G1 and G2 may also be configured to align with each other at the side seams 178, 180 to provide the appearance of a contiguous design that extends across the side seams 178, 180.

As discussed above with reference to FIGS. 4A4 and 4B4, during the assembly process, elastic material in the first and/or second belts 106, 108 and/or the chassis 102 may be positioned in an absorbent article 100 under tension and may be held under tension during the assembly process. However, such tension on the elastic material may be removed before or during the assembly process, allowing the elastic material in the first and/or second belts 106, 108 and/or the chassis 102 to contract. As such, the first belt 106, the second belt 108, and/or the chassis 102 shown in FIGS. 7G1 and 7G2 may be advanced in the machine direction MD under tension. However, such tension may be removed, thus allowing elastic material to deform the first and/or second belts 106, 108 and/or the chassis 102 so as to cause the first region 502 (or first graphic G1), second region 504 (or second graphic G2), and/or third region 506 (or chassis graphic Gc) of the design 500 to intersect or mate so as to form a contiguous design across the chassis 102 and the first belt 106 and/or across the chassis 102 and the second belt 108, such as described above with reference to FIGS. 4A4 and 4B4. For example, tension on the elastic material may be removed immediately after advancing from the cutting apparatus 338.

Figure 8:
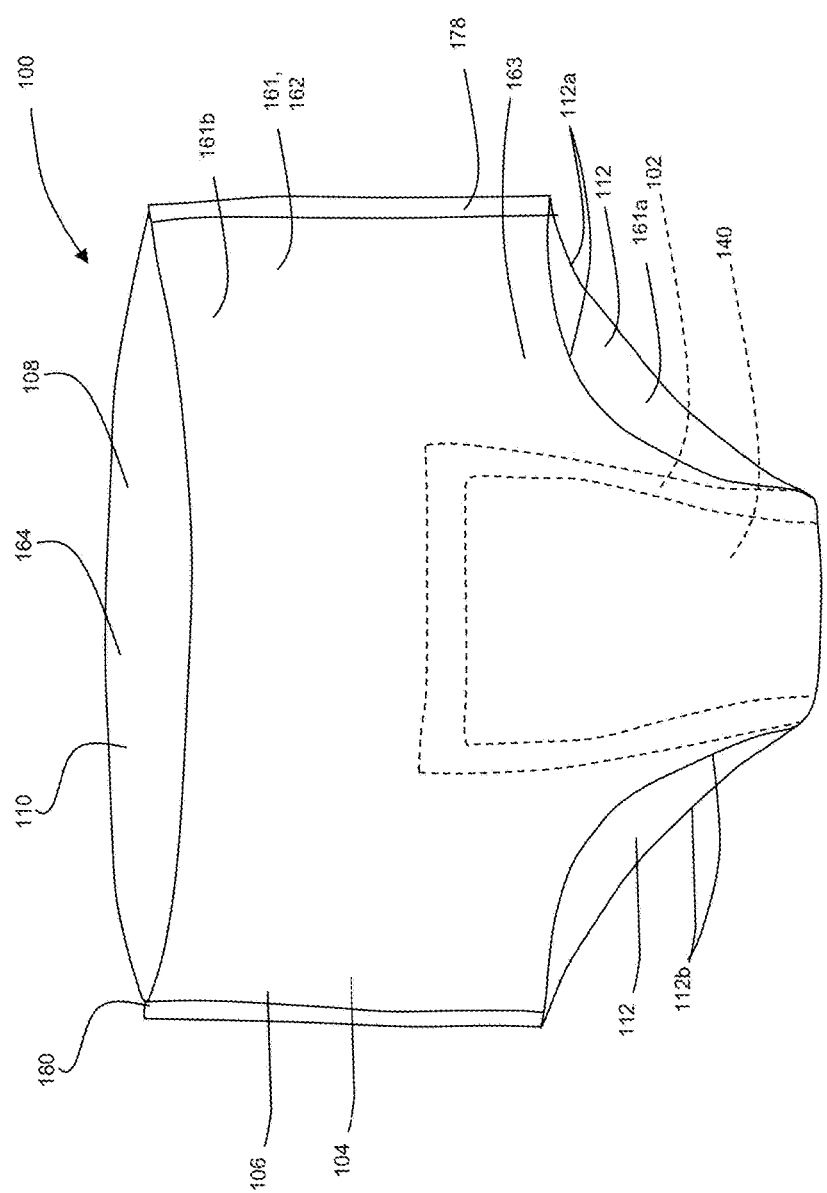
FIG. 8 is a front perspective view of a diaper pant constructed with a contiguous outer cover.
Figure 9:
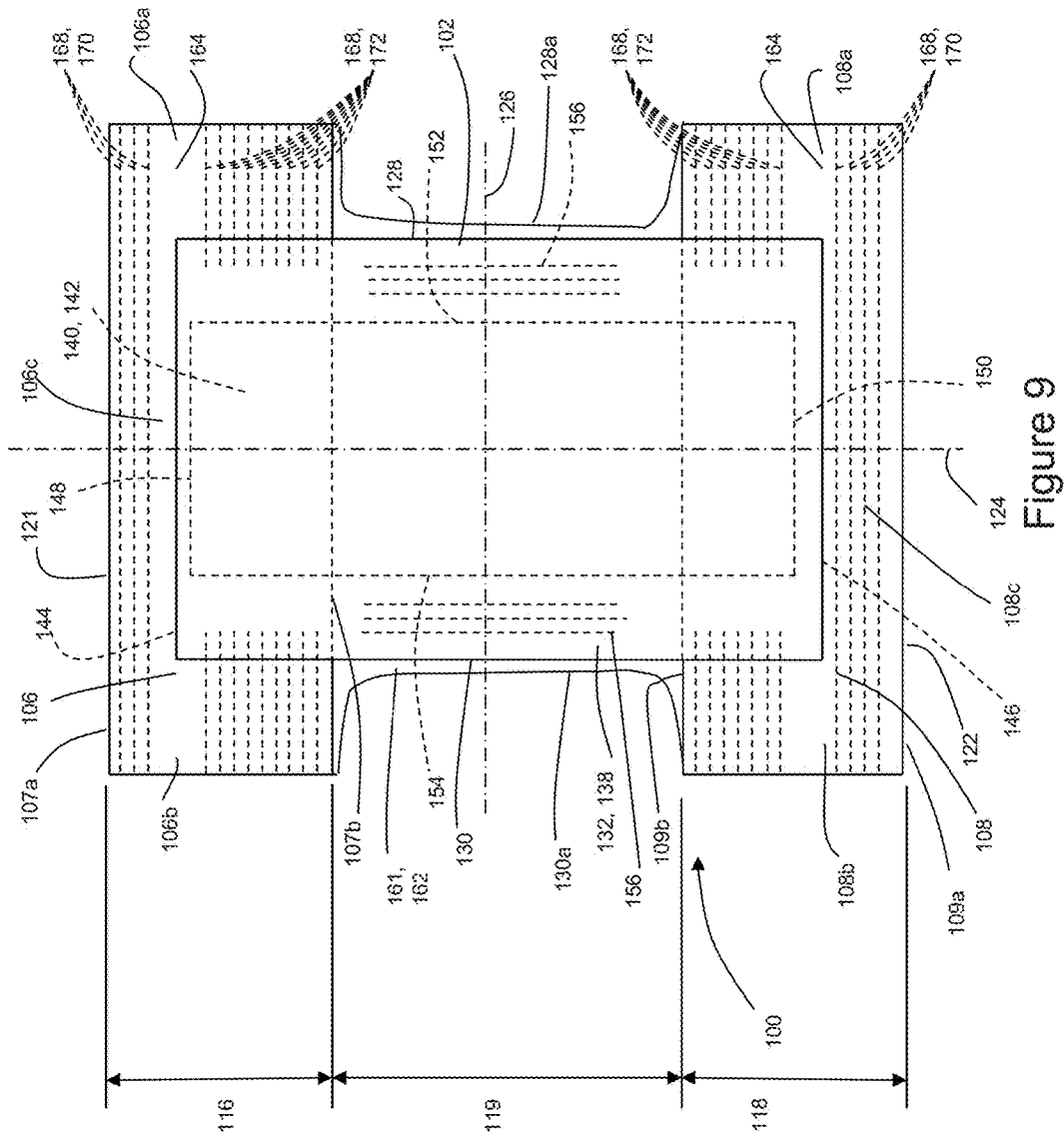
FIG. 9 is a partially cut away plan view of the diaper pant shown in FIG. 8 in a flat, uncontracted state.

As previously mentioned, it is to be appreciated that the various types of diaper pants 100 may be assembled with the graphics G1, G2, Gc and associated discontinuous regions 508, 510 discussed above. Some embodiments of the diaper pants 100 may include a chassis 102 and elastic belts 106, 108 configured in different ways other than as depicted in FIGS. 1A-2B. For example, FIGS. 8 and 9 show a diaper pant 100 having many of the same components as described above with reference to FIGS. 1A-2B, except the outer layer 162 of the elastic belts 106, 108 is configured as a contiguous outer cover 161 that extends through the first waist region 116, crotch region 119, and second waist region 118. Thus, as shown in FIG. 9, the outer cover 161 also includes a first waist end region 116, a crotch region 119, and an opposing second waist end region 118. The outer cover 161 also includes a garment facing surface 161b and an opposing wearer facing surface 161a. The first and second elastic belts 106, 108 may also each include belt elastic material 168 interposed between the outer cover 161 and the inner substrate layer 164. As such, elastic members 168 of the elastic belts 106, 108 may be connected with the wearer facing surface 161a of the outer cover 161. And the chassis 102 may be positioned on the wearer facing surface 161a of the outer cover 161. As such, the backsheet 136 may include a portion of the outer cover 161. In addition, the outer cover 161 may include a first longitudinal side edge 128a and a second longitudinal side edge 130a that are positioned laterally outboard the first longitudinal side edge 128 of the chassis 102 and second longitudinal side edge 130 of the chassis 102, respectively, as shown in FIG. 9. As shown in FIGS. 8 and 9, the first longitudinal side edge 128a may define the perimeter 112a of one leg opening 112, and the second longitudinal side edge 130a may define the perimeter 112b of the other leg opening 112. It is to be appreciated also that the first longitudinal side edge 128a and a second longitudinal side edge 130a may aligned with or positioned laterally inboard of the first longitudinal side edge 128 of the chassis 102 and second longitudinal side edge 130 of the chassis 102, respectively. As such, in some embodiments, the perimeter 112a of one leg opening 112 may be defined by portions of the first longitudinal edges 128, 128a, and the perimeter 112b of the other leg opening may be defined by portions of the second longitudinal edges 130, 130a.

Figure 10A:
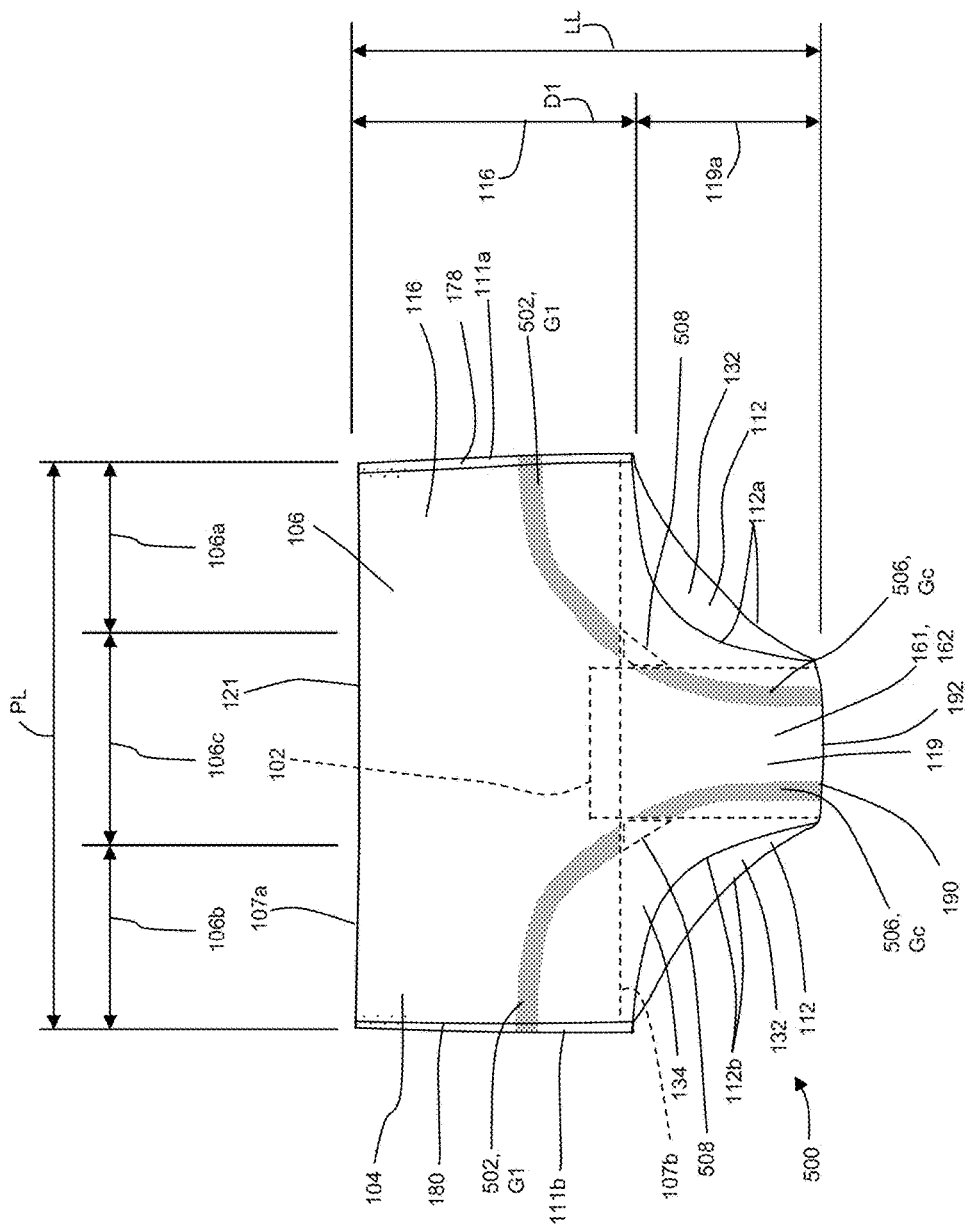
FIG. 10A is a front plan view of the diaper pant in FIG. 8 and including a design extending across a first belt and a chassis.
Figure 10B:
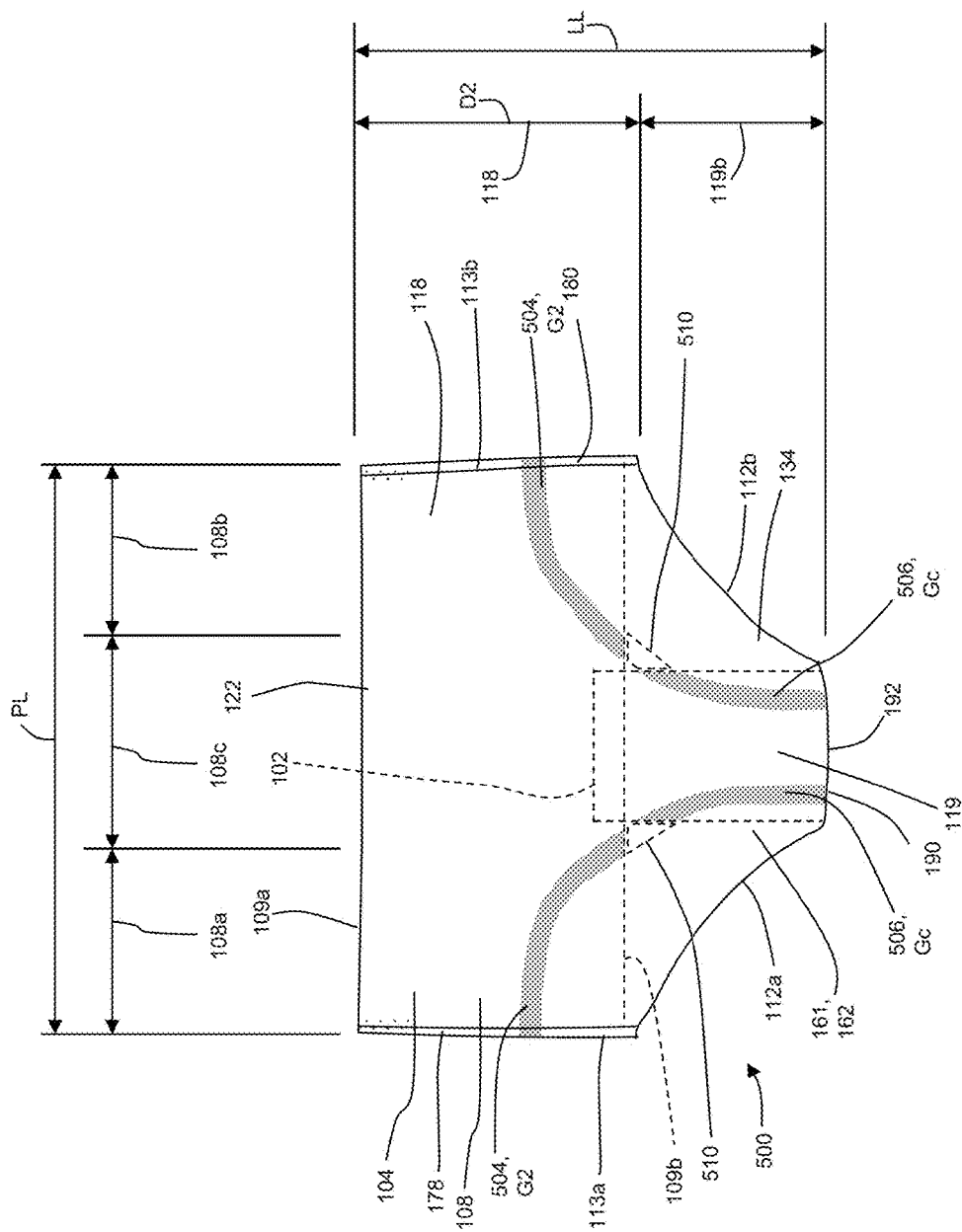
FIG. 10B is a rear plan view of the diaper pant of FIG. 10A and including a design extending across a second belt and the chassis.

FIG. 10A shows a front plan view of a diaper pant 100 in a laid flat condition illustrating various regions of the diaper pant 100. And FIG. 10B shows a rear plan view of the diaper pant 100 in a laid flat condition illustrating various regions of the diaper pant 100. As discussed above, the diaper pant 100 defines include an inner, body facing surface 132, and an outer, garment facing surface 134. The diaper pant 100 also includes a crotch end 190 that is defined by a lateral fold line 192 in the crotch region 119. As such, the lateral fold line 192 divides the crotch region into a first crotch region 119a and a second crotch region 119b.

The diaper pant 100 is shown in FIGS. 8-10B as having a first elastic belt 106, and a second elastic belt 108. The first belt 106 has a first end region 106a, an opposing second end region 106b, and a central region 106c. And the second belt 108 has a first end region 108a, an opposing second end region 108b, and a central region 108c. The first end regions 106a, 108a are connected together at a first side seam 178, and the second end regions are 106b, 108b are connected together at a second side seam 180. As shown in FIGS. 10A and 10B, the distance between the first longitudinal side edge 111a and the second longitudinal side edge 111b defines the pitch length, PL, of the first elastic belt 106, and the distance between the first longitudinal side edge 113a and the second longitudinal side edge 113b defines the pitch length, PL, of the second elastic belt 108.

The first end region 106a the first belt 106 may extend approximately 20% to 40% of the pitch length PL of the diaper pant 100 in an assembled, laid-flat, relaxed condition, and the first end region 108a the second belt 108 may extend approximately 20% to 40% of the pitch length PL of the diaper pant 100 in an assembled, laid-flat, relaxed condition. The second end region 106b the first belt 106 may extend approximately 20% to 40% of the pitch length PL of the diaper pant 100 in an assembled, laid-flat, relaxed condition, and the second end region 108b the second belt 108 may extend approximately 20% to 40% of the pitch length of the diaper pant 100 in an assembled, laid-flat, relaxed condition. The central region 106c the first belt 106 may extend approximately 20% to 60% of the pitch length PL of the diaper pant 100 in an assembled, laid-flat, relaxed condition, and the central region 108c the second belt 108 may extend approximately 20% to 60% of the pitch length PL of the diaper pant 100 in an assembled, laid-flat, relaxed condition.

The diaper pant 100 in FIGS. 10A and 10B is also shown as having a longitudinal length LL that is defined by the distance between the first waist edge 121 and the crotch end 190 (or the lateral fold line 192), or if longer, the distance from the second waist edge 122 to the crotch end 190 (or the lateral fold line 192). The longitudinal length LL may be measured along the longitudinal centerline 124 of the diaper pant 100. As shown in FIGS. 10A-10B, the first waist region 116 extends a distance D1 generally in the longitudinal direction from the waist edge 121 along the side seams 178, 180 to the perimeter edges 112a, 112b of leg openings 112, and the second waist region 118 extends a distance D2 generally in the longitudinal direction from the waist edge 122 along the side seams 178, 180 to the perimeter edges 112a, 112b of leg openings 112. Hence, a first crotch region 119a extends a distance from the crotch end 190 to the first waist region 116, and a second crotch region 119b extends a distance from the crotch end 190 to the second waist region 118. In some embodiments, the first waist region 116 and/or the second waist region 118 may extend about two-thirds the longitudinal length LL of the assembled diaper pant 100. In addition, the first crotch region 119a and/or the second crotch region 119b may extend about one-third the longitudinal length LL of the assembled diaper pant 100.

Similar to the embodiment discussed above with reference to FIGS. 1A-5C, the diaper pant 100 shown in FIGS. 10A and 10B also includes a design 500 extending across the first elastic belt 106, the second elastic belt 108, and the chassis 102. As discussed above, the design 500 may include a first region 502, a second region 504, a third region 506, a first discontinuous region 508, and a second discontinuous region 510. And the first region 502 comprises a first graphic G1 printed directly on the first elastic belt 106; the second region 504 comprises a second graphic G2 printed directly on the second elastic belt 108; and the third region 506 comprises a chassis graphic Gc printed on the chassis 102. As such, the discontinuous regions 508, 510 may be configured as discussed above with reference to FIGS. 4A1-4A3 and 4B1-4B3.

It is to be appreciated the first graphic G1 may be printed on the inner substrate layer 164 of the first belt 106 and may be visible through the outer cover 161, and/or the second graphic G2 may be printed on the inner substrate layer 164 of the second belt 108 and may be visible through the outer cover 161. And the chassis graphic Gc may be printed on various components of the chassis 102 as discussed above. In some embodiments, the first graphic G1, the second graphic G2, and/or the chassis graphic Gc may be printed on the garment facing surface 161b and/or the opposing wearer facing surface 161a of the outer cover 161.

It is to be appreciated that the methods of assembly of diaper pants specifically described herein and illustrated in the accompanying drawings are non-limiting example embodiments. The features illustrated or described in connection with one non-limiting embodiment may be combined with the features of other non-limiting embodiments. Such modifications and variations are intended to be included within the scope of the present disclosure.

Packages

It is also to be appreciated that absorbent articles comprising graphics according to the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 110 mm, less than about 100 mm, less than about 80 mm, less than about 78 mm, or less than about 76 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 68 mm to about 110 mm or from about 72 mm to about 80 mm or from about 74 mm to about 78 mm, specifically reciting all 0.1 mm increments within the specified ranges and all ranges formed therein or thereby, according to the In-Back Stack Height Test described herein.

Figure 11:
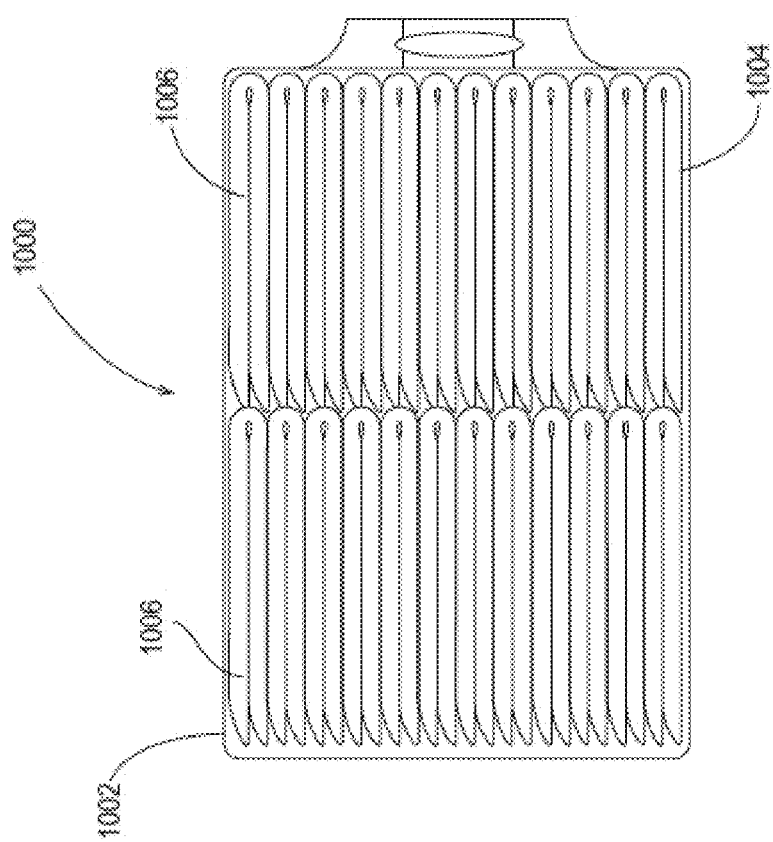
FIG. 11 is a side view of a package of absorbent articles showing the package width, and wherein the outer surface of the package is illustrated as transparent for purposes of clarity.

FIG. 11 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e., each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 11). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assembling disposable diaper pants, each diaper pant comprising a chassis having a first end region and an opposing second end region separated from each other by a central region, and having a longitudinal axis and a lateral axis, the chassis comprising: a topsheet, a backsheet, and an absorbent core disposed between the topsheet and the backsheet, the method comprising the steps of:

advancing a first continuous elastic laminate in a machine direction comprising an outer longitudinal edge and an inner longitudinal edge defining a width in a cross direction, the first continuous elastic laminate comprising a printed belt substrate comprising a first graphic, the first graphic extending in the machine direction and the cross direction and comprising an end edge adjacent a longitudinal edge of the printed belt substrate, the end edge having a width defined by a distance extending in the machine direction between a first side edge of the first graphic and a second side edge of the first graphic;

advancing a second continuous elastic laminate comprising an outer longitudinal edge and an inner longitudinal edge;

advancing a chassis in the machine direction, the chassis comprising a first side edge and a second side edge separated from the first side edge in the machine direction, the chassis comprising a printed chassis substrate comprising a second graphic comprising an end edge extending in the cross direction and adjacent a side edge of the printed chassis substrate, the end edge comprising a length defined by a distance extending between a first side edge of the second graphic and a second side edge of the second graphic; and positioning the chassis onto the first continuous elastic laminate and the second continuous elastic laminate to define a discontinuous region devoid of printing and separating the first graphic from the second graphic, the discontinuous region defined by a substantially trapezoidal-shaped perimeter extending between the end edge of the first graphic and the end edge of the second graphic, defining an imaginary continuous extension of an established direction of the first graphic to the second graphic.

2. The method of claim 1, further comprising the step of: folding the chassis along the lateral axis to position the first continuous elastic laminate into a facing relationship with the second continuous elastic laminate.

3. The method of claim 1, further comprising the step of: cutting the first and second continuous elastic laminates in the cross direction to form discrete diaper pants.

4. The method of claim 1, further comprising the steps of:
advancing a continuous length of chassis in a machine direction; and
cutting the continuous length of chassis in a cross direction to form a discrete chassis.

5. The method of claim 1, wherein the printed chassis substrate is a backsheet of the chassis and wherein the end edge of the second graphic is positioned laterally inboard of the first side edge of the chassis.

6. The method of claim 1, wherein the first continuous elastic laminate further comprises a second substrate, and wherein the printed belt substrate comprises a first surface and an opposing second surface, and the second substrate comprises a first surface and an opposing second surface, and wherein elastic material is bonded between the first surfaces of the printed belt substrate and the second substrate.

7. The method of claim 6, wherein the first graphic is printed on the first surface of the printed belt substrate.

8. A method for assembling disposable diaper pants, each diaper pant comprising a chassis having a first end region and an opposing second end region separated from each other by a central region, and having a longitudinal axis and a lateral axis, the chassis comprising: a topsheet, a backsheet, and an absorbent core disposed between the topsheet and the backsheet, the method comprising the steps of:
advancing an elastic laminate in a machine direction, the elastic laminate comprising a first longitudinal edge and a second longitudinal edge, the elastic laminate further comprising a first graphic extending in the machine direction and the cross direction;
cutting the elastic laminate along the machine direction and through the graphic to form a first elastic laminate comprising a first portion of the first graphic and a second elastic laminate comprising a second portion of the first graphic, wherein the first and second elastic laminates each include an inner longitudinal edge and an outer longitudinal edge, wherein the first portion of the first graphic comprises an end edge coincident with the inner longitudinal edge of the first elastic laminate, and wherein the second portion of the first graphic comprises an end edge coincident with the inner longitudinal edge of the second elastic laminate;
separating the first elastic laminate in the cross direction from the second elastic laminate to define a gap between the inner longitudinal edge of the first elastic laminate and the inner longitudinal edge of the second elastic laminate;
advancing a chassis in the machine direction, the chassis including a first side edge and a second side edge separated from the first side edge in the machine direction, wherein the chassis comprises a printed chassis substrate comprising a second graphic comprising a first end edge and a second end edge each extending in the cross direction and adjacent a side edge of the printed chassis substrate; and
positioning the chassis across the gap and onto the first elastic laminate to define a first discontinuous region devoid of printing and separating the first portion of the first graphic from the second graphic, the discontinuous region defined by a substantially trapezoidal-shaped perimeter extending between the end edge of the first portion of the first graphic and the first end edge of the second graphic.

9. The method of claim 8, further comprising the step of: positioning the chassis onto the second elastic laminate to define a second discontinuous region devoid of printing and separating the second portion of the first graphic from the second graphic, the discontinuous region defined by a substantially trapezoidal-shaped perimeter extending between the end edge of the first portion of the first graphic and the second end edge of the second graphic.

10. The method of claim 8, further comprising the step of: folding the chassis along the lateral axis to position the first elastic laminate into a facing relationship with the second elastic laminate.

11. The method of claim 8, further comprising the step of: cutting the first and second elastic laminates in the cross direction to form discrete diaper pants.

12. The method of claim 8, further comprising the steps of:
advancing a continuous length of chassis in a machine direction; and
cutting the continuous length of chassis in a cross direction to form a discrete chassis.

13. The method of claim 8, wherein the printed chassis substrate comprises a backsheet of the chassis.

14. The method of claim 8, wherein the elastic laminate comprises a first substrate having a first surface and an opposing second surface, a second substrate having a first surface and an opposing second surface, and elastic material bonded between the first surfaces of the first and second substrates.

15. The method of claim 14, wherein the first graphic is printed on the first surface of the first substrate.

16. The method of claim 8, further comprising the steps of:
advancing the first elastic laminate under tension; and
removing the tension to form a contiguous design by mating the first graphic and the second graphic upon contraction of the first elastic laminate.

\* \* \* \* \*